US011034960B2

(12) United States Patent
Mardinoglu et al.

(10) Patent No.: US 11,034,960 B2
(45) Date of Patent: Jun. 15, 2021

(54) PKLR INHIBITION IN THE TREATMENT OF NAFLD AND HCC

(71) Applicant: ScandiEdge Therapeutics AB, Johanneshov (SE)

(72) Inventors: Adil Mardinoglu, Gothenburg (SE); Jan Borén, Gothenburg (SE); Mathias Uhlén, Stockholm (SE)

(73) Assignee: ScandiEdge Therapeutics AB, Johanneshov (SE)

( * ) Notice: Subject to any disclaimer, the term of this patent is extended or adjusted under 35 U.S.C. 154(b) by 0 days.

(21) Appl. No.: 16/638,927

(22) PCT Filed: Aug. 14, 2018

(86) PCT No.: PCT/EP2018/072036

§ 371 (c)(1),
(2) Date: Feb. 13, 2020

(87) PCT Pub. No.: WO2019/034657

PCT Pub. Date: Feb. 21, 2019

(65) Prior Publication Data

US 2020/0190523 A1 Jun. 18, 2020

(30) Foreign Application Priority Data

Aug. 14, 2017 (EP) .................................... 17186181

(51) Int. Cl.
*A61K 48/00* (2006.01)
*C12N 15/11* (2006.01)
*C07H 21/02* (2006.01)
*C07H 21/04* (2006.01)
*C12N 15/113* (2010.01)

(52) U.S. Cl.
CPC ...... *C12N 15/1137* (2013.01); *C12N 2310/11* (2013.01); *C12N 2310/14* (2013.01); *C12N 2310/141* (2013.01); *C12N 2310/312* (2013.01); *C12N 2310/315* (2013.01); *C12N 2310/351* (2013.01)

(58) Field of Classification Search
CPC ..... A61K 31/713; A61K 31/7105; A61P 1/16; A61P 35/00; C12N 15/1137; C12N 2310/11
See application file for complete search history.

(56) References Cited

U.S. PATENT DOCUMENTS

2011/0212889 A1 9/2011 Oral et al.

FOREIGN PATENT DOCUMENTS

WO 2011/115810 9/2011

OTHER PUBLICATIONS

Krishnan et al. (Cell Systems, 2018 vol. 6:103-115).*
(Continued)

*Primary Examiner* — Terra C Gibbs
(74) *Attorney, Agent, or Firm* — Myers Bigel, P.A.

(57) ABSTRACT

There is provided a medical agent for use in a method of treatment of nonalcoholic fatty liver disease (NAFLD) or hepatocellular carcinoma (HCC), wherein the medical agent comprises a polynucleotide and is capable of silencing or knocking out the PKLR gene.

23 Claims, 6 Drawing Sheets

Specification includes a Sequence Listing.

PKLR PNPLA3 PCSK9
TPM
800 600 400 200 0
35 30 25 20 15 10 5 0
150 100 50 0
High FASN Low FASN High FASN Low FASN High FASN Low FASN

(56) References Cited

OTHER PUBLICATIONS

Agren et al. "Identification of anticancer drugs for hepatocellular carcinoma through personalized genome-scale metabolic modeling", Molecular Systems Biology 10(3):721 (2014) (13 pages).
International Search Report and Written Opinion corresponding to International Application No. PCT/EP2018/072036 dated Sep. 25, 2018.
Lee et al. "Network analyses identify liver-specific targets for treating liver diseases", Molecular Systems Biology 13(8):938 (2017) (15 pages).
Nair et al. "Multivalent N-Acetylgalactosamine-Conjugated siRNA Localizes in Hepatocytes and Elicits Robust RNAi-Mediated Gene Silencing", J. Am. Chem. Soc. 136(49):16958-16961 (2014).
Prakash et al. "Synergistic effect of phosphorothioate, 5'-vinylphosphonate and GaINAc modificaiions for enhancing activity of synthetic siRNA", Bioorganic & Medicinal Chemistry Letters 26(12):2817-2820 (2016).

* cited by examiner

PKLR INHIBITION IN THE TREATMENT OF NAFLD AND HCC

STATEMENT OF PRIORITY

This application is a 35 U.S.C. § 371 national phase application of PCT Application No. PCT/EP2018/072036 filed Aug. 14, 2018, which claims priority to European Application No. 17186181.8 filed Aug. 14, 2017, the entire contents of each of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 9868-88_ST25.txt, 13,136 bytes in size, generated on Jan. 29, 2020 and filed via EFS-Web, is provided in lieu of a paper copy. This Sequence Listing is hereby incorporated by reference into the specification for its disclosures.

TECHNICAL FIELD

The invention relates to treatment of non-alcoholic fatty liver disease (NAFLD) and hepatocellular carcinoma (HCC).

BACKGROUND

Non-alcoholic fatty liver disease (NAFLD) is characterized by the accumulation of excess fat in the liver and is associated with obesity, insulin resistance (IR) and type 2 diabetes (T2D). NAFLD includes a spectrum of diseases ranging from simple steatosis to nonalcoholic steatohepatitis (NASH) and plays a major role in the progression of cirrhosis and hepatocellular carcinoma (HCC), a cancer with one of the highest mortality rates worldwide (Kew, 2010). Although NAFLD is the most common cause of chronic liver disease in developed countries, and its worldwide prevalence continues to increase along with the growing obesity epidemic, there is no approved pharmacological treatment for NAFLD. NAFLD is projected to become the most common indication leading to liver transplantation in the United States by 2030 (Shaker et al, 2014). The incidence of HCC has also increased significantly in the United States over the past few decades, in parallel with the epidemic of NAFLD (Petrick et al, 2016). Hence, there is an urgent need to develop new strategies for preventing and treating such chronic hepatic diseases.

Biological networks can be used to uncover complex systems-level properties. Systems biology combining experimental and computational biology to decipher the complexity of biological systems can be used for the development of effective treatment strategies for NAFLD, HCC and other complex diseases (Mardinoglu et al, 2017b; Mardinoglu & Nielsen, 2015; Nielsen, 2017; Yizhak et al, 2015). To date, several metabolic processes that are altered in NAFLD (Hyötyläinen et al, 2016; Mardinoglu et al, 2014a; Mardinoglu et al, 2017a) and HCC (Agren et al, 2012; Agren et al, 2014; Björnson et al, 2015; Elsemman et al, 2016) have been revealed through the use of genome-scale metabolic models (GEMs), a popular tool in systems biology. GEMs are reconstructed on the basis of detailed biochemical information and have been widely used to determine the underlying molecular mechanisms of metabolism-related disorders, including NAFLD, HCC and type 2 diabetes (Björnson et al, 2015; Bordbar et al, 2014; Mardinoglu et al, 2013b; Mardinoglu & Nielsen, 2012; Mardinoglu & Nielsen, 2015; Mardinoglu & Nielsen, 2016; Mardinoglu et al, 2015; O'Brien et al, 2015; Shoaie et al, 2015; Uhlen et al, 2016; Yizhak et al, 2013; Yizhak et al, 2014a; Yizhak et al, 2014b; Zhang et al, 2015).

Recently, GEMs for hepatocytes (iHepatocytes2322) (Mardinoglu et al, 2014a), myocytes (iMyocytes2419) (Varemo et al, 2015) and adipocytes (iAdipocytes1850) (Mardinoglu et al, 2013a; Mardinoglu et al, 2014b) have been integrated with transcriptional regulatory networks (TRNs) and protein-protein interaction networks (PPINs) to generate tissue-specific integrated networks (INs) for liver, muscle and adipose tissues (Lee et al, 2016). The INs allows comprehensive exploration of the tissue biological processes altered in the liver and adipose tissues of obese subjects, thus accounting for the effects of transcriptional regulators and their interacting proteins and enzymes. Although INs provides physical interactions between pairs or groups of enzymes, transcription factors (TFs) and other proteins, these physical interactions may not necessarily have close functional connections.

SUMMARY

Co-expression connections are enriched for functionally related genes, and co-expression networks (CNs) allow the simultaneous investigation of multiple gene co-expression patterns across a wide range of clinical and environmental conditions. In the study behind the present invention, CNs were constructed for 46 major human tissues including liver, muscle and adipose tissues and the overlap between functional connections and physical interactions defined by CNs and INs, respectively, was studied. Also, CNs for HCC were constructed to investigate the functional relationship between genes. Finally, these comprehensive biological networks were used to explore the altered biological processes in NAFLD and HCC, and a liver-specific gene target that can be silenced for treatment of NAFLD and HCC (with likely minimal negative side effects) was identified.

Compared to other tissues, it is relatively easy to target liver tissue with a polynucleotide drug, such as a drug comprising siRNA or an antisense oligonucleotide; hepatocytes are highly receptive to uptake of such drugs (Dowdy (2017)). This is due to several factors, including the blood flow to the liver, rapid endocytosis, discontinuous endothelium and high receptor expression level (Khvorova et al. (2017); Dowdy (2017)). Further, there are multiple designs that enhance the targeting of the liver (see e.g. Khvorova et al. (2017).

The present disclosure thus provides, in a first aspect, a medical agent for use in a method of treatment of nonalcoholic fatty liver disease (NAFLD) or hepatocellular carcinoma (HCC), wherein the medical agent comprises a polynucleotide and is capable of silencing or knocking out the PKLR gene.

There are two transcripts of the PKLR gene: PKLR-201 (Transcript ID ENST00000342741.4); and PKLR-202 (Transcript ID ENST00000392414.7). The cDNA sequence of PKLR-201 is referred to herein as SEQ ID NO:1. The coding sequence of PKLR-201 is referred to herein as SEQ ID NO:2. The cDNA sequence of PKLR-202 is referred to herein as SEQ ID NO:3. The coding sequence of PKLR-202 is referred to herein as SEQ ID NO:4.

In the context of the present disclosure, a "polynucleotide" refers to a molecular chain of nucleotides chemically bonded by a series of ester linkages between the phosphoryl group of one nucleotide and the hydroxyl group of the sugar in the adjacent nucleotide. The term "polynucleotide" thus encompass "oligonucleotide". Typically, the polynucleotide of the present disclosure comprises at least six nucleotides, such as at least ten or twelve nucleotides.

Oligonucleotide therapeutics comprise a diverse class of drugs, including small interfering RNAs (siRNAs), antisense oligonucleotides (ASOs), microRNAs (miRNAs) and aptamers (see e.g. Khvorova et al. (2017)).

The polynucleotide of the first aspect may be an RNA molecule, such as a small interfering RNA (siRNA) molecule, microRNA (miRNA) molecule, a guide RNA molecule (gRNA) or an aptamer.

When the RNA molecule is a gRNA molecule, the medical agent may be a CRISPR/Cas9 agent or a RNA-targeting Cas9 (RCas9) agent (see e.g. Batra et al. (2017).

Further, the polynucleotide of the first aspect may be an antisense polynucleotide, such as an antisense oligonucleotide (ASO). The ASO may be a DNA sequence, a RNA sequence or a chemical analogue.

The polynucleotide is preferably capable of selective interaction with PKLR DNA or PKLR RNA. The polynucleotide may thus be capable of selective interaction with a sequence selected from SEQ ID NO: 1, 2, 3 and 4 or with a RNA sequence that can be transcribed from SEQ ID NO: 1, 2, 3 or 4, preferably from SEQ ID NO: 2 or 4.

In one embodiment, the polynucleotide is an antisense siRNA or AON strand that is capable of selective interaction with PKLR mRNA that can be transcribed from SEQ ID NO: 1, 2, 3 or 4, preferably from SEQ ID NO: 2 or 4.

In the present disclosure, two different siRNAs are used for silencing PKLR. For the first one (referred to as "siRNA 53" below), the sense sequence is SEQ ID NO:5 and the antisense sequence is SEQ ID NO:6. For the second one (referred to as "siRNA 54" below), the sense sequence is SEQ ID NO:7 and the antisense sequence is SEQ ID NO:8.

In embodiments of the first aspect, the polynucleotide of the medical agent may thus comprise a sequence that is at least 75% identical to SEQ ID NO:5, SEQ ID NO:6, SEQ ID NO:7 or SEQ ID NO:8, preferably at least 75% identical to one of the antisense sequences SEQ ID NO: 6 and SEQ ID NO:6.

In more limited embodiments of the first aspect, the polynucleotide of the medical agent may thus comprise a sequence that is at least 85% identical to SEQ ID NO:5, SEQ ID NO:6, SEQ ID NO:7 or SEQ ID NO:8, preferably at least 85% identical to one of the antisense sequences SEQ ID NO: 6 and SEQ ID NO:8.

In even more limited embodiments of the first aspect, the polynucleotide of the medical agent may thus comprise a sequence that is at least 95% identical to SEQ ID NO:5, SEQ ID NO:6, SEQ ID NO:7 or SEQ ID NO:8, preferably at least 95% identical to one of the antisense sequences SEQ ID NO: 6 and SEQ ID NO:8.

The term "% identical", as used in the context of the present disclosure, is calculated as follows. The query sequence is aligned to the target sequence according to the CLUSTAL W algorithm (Thompson, J. D., Higgins, D. G. and Gibson, T. J., Nucleic Acids Research, 22: 4673-4680 (1994)). The nucleotides at each position are compared, and the percentage of positions in the query sequence that have identical correspondences in the target sequence is reported as % identical. Also, the target sequence determines the number of positions that are compared. Consequently, in the context of the present disclosure, a query sequence that is shorter than the target sequence can never be 100% identical to the target sequence. For example, a query sequence of 85 amino acids may at the most be 85% identical to a target sequence of 100 amino acids.

In one embodiment of the first aspect, the polynucleotide comprises a sequence selected from SEQ ID NO:5, SEQ ID NO:6, SEQ ID NO:7 and SEQ ID NO:8.

The medical agent of the first agent may benefit from a delivery agent, in particular when the polynucleotide is a siRNA (Dowdy (2017)). Examples of delivery agents are lipid nanoparticles (LNPs) and synthetic nanoparticles that were originally designed for DNA-mediated gene therapy. These LNPs were retooled and optimized for siRNA delivery using ionizable lipids that effectively lowered the dose 100-fold from ~1 mg/kg to 0.01 mg/kg for liver target genes ((Dowdy (2017); (Akinc et al. (2008); Semple, et al. (2010); Love et al. (2010)). An example of a LNP siRNA formulation for delivery to the liver is a drug tested by Alnylam in phase 3 clinical trial that targets liver transthyretin amyloidosis (TTR) (Dowdy (2017)).

A single LNP can potentially deliver a hundred siRNAs. A LNP 100 nm in diameter is ~100 megaDa in size or some 5,000× larger than a approximately 14 kDa siRNA drug being delivered (Dowdy (2017)). The LNP size may result in a poor diffusion coefficient and poor pharmacokinetics that, due to the hepatocyte's space of Disse architecture, predominantly targets liver.

The medical agent of the first aspect may thus be formulated in a lipid nanoparticle (LNP). For example, the diameter of the LNP may be 10-500 nm, such as 40-250 nm.

Conjugate-mediated delivery is an alternative to lipids in the delivery toolbox (Khvorova et al. (2017); Juliano (2016)). GalNAc conjugates can be applied to all types of polynucleotide/oligonucleotide therapeutics to treat liver diseases (Khvorova et al. (2017)).

The concept of using trivalent GalNAc clusters for drug delivery to hepatocytes, which are the cells of the main parenchymal tissue of the liver, was first shown in 1987 (Juliano (2016)), and for oligonucleotide delivery in 1995, but the GalNAc-conjugated oligonucleotides reached clinical acceptance more recently (Khvorova et al. (2017); Nair et al. (2014)).

GalNAc siRNA (Nair (2014); Matsuda et al. (2015); Rajeev et al. (2015); Sehgal, A. et al. (2015)) and ASO (Prakash et al. (2014); Yu et al. (2016a); Yu et al. (2016b)) are thus options for silencing in hepatocytes using therapeutic polynucleotides/oligonucleotides. Blood flow to the liver, discontinuous endothelium, and high receptor expression level all work together to achieve sufficient uptake and support multi-month efficacy with a single injection (Khvorova et al. (2017)). Trivalent GalNAc conjugates may be of particular interest for hepatocytes, given the wide therapeutic index and excellent safety profile of these compounds (Khvorova et al. (2017)). It has been reported that more than three GalNAc molecules per ASO drives preferential delivery to liver (Khvorova et al. (2017); Makila et al. (2014)). Oral administration, e.g. daily, or subcutaneous injections, e.g. monthly or quarterly, are two possible ways of administration (Khvorova et al. (2017)).

Conjugation of N-acetyl galactosamine (GalNAc) enables the conjugate to bind to the asialoglycoprotein receptor (ASGPR), which are highly abundant on hepatocytes. The GalNAc conjugation thus increases delivery into hepatocytes (Dowdy (2017); Prakash (2014)).

A number of embodiments follow from the discussion above.

In an embodiment of the medical agent of the first aspect, the oligonucleotide is conjugated to GalNAc, such as a GalNAc cluster. The oligonucleotide-GalNAc conjugate may be a trivalent GalNAc conjugate. Further, the oligonucleotide-GalNAc conjugate may comprise more than three GalNAc molecules per oligonucleotide.

The polynucleotide may be modified to improve metabolic stability. Such a modification is of particular interest is case of administration by subcutaneous injection, e.g. monthly, quarterly or semiannually.

For example, the 5'-phosphate of the polynucleotide of the first aspect may be modified, e.g. to 5'-vinylphosphonate (see e.g. Prakash et al. (2016)).

Further, the polynucleotide of the first aspect may be phosphorothioate modified (see e.g. Prakash et al. (2016)). Interestingly, the presence of phosphorothioate bonds enhances the potency of GalNAc-delivered siRNAs (Prakash (2016)).

Such modified polynucleotides have show exception stability and duration of effect, particularly if they are also GalNAc-conjugated (Khvorova et al. (2017); Prakash et al. (2016)).

In an embodiment of the first aspect, the medical agent is administered orally or by subcutaneous injection.

To improve the chances of a successful treatment, the expression of PKLR in the patient's liver may be checked before the medical agent is administrated. If the PKLR expression is found to be absent or at a low level, it may be decided to refrain from treating the patient with the medical agent.

In an embodiment of the first aspect, the method thus comprises a step of detecting expression of the PKLR gene in a liver sample, preferably a liver tissue sample, from the subject having the NAFLD or HCC. The step is typically carried out ex vivo. The liver sample is typically a liver biopsy, preferably a liver biopsy taken earlier for diagnosing the patient.

Methods of detecting the expression of the PKLR gene are known to the skilled person and comprise PCR, RNA-Seq and micro array methods.

The inventors have found that the PKLR expression is typically upregulated in cancerous liver tissue, but that the PKLR expression is often significantly decreased (to levels below those that are typical for healthy tissue) in an advanced stage when the liver is no longer functional and the patient is not particularly responsive to treatment. Accordingly, patients that exhibit relatively high PKLR expression are particularly suited for the treatment of the present disclosure. Here, "relatively high PKLR expression" means an expression level that is higher than a relevant reference level. Such a relevant reference level may for example be a value obtained from measurements in healthy liver tissue. Accordingly, the decision may be to give the treatment if the PKLR expression is higher than "normal" PKLR expression in healthy liver tissue. Alternatively, the relevant reference level may be a value obtained from measurements in advanced stage cancerous tissue, e.g. from failed livers. In such case, decision may thus be to give the treatment if the PKLR expression level is higher than a level representative of terminal disease.

In one embodiment, the above-mentioned detection step may thus result in a PKLR expression level that is compared to a relevant reference level (as discussed above) and if the PKLR expression level is higher than the relevant reference level, the medical agent is administered.

As a second aspect of the present disclosure, there is provided a method of treating a subject having nonalcoholic fatty liver disease (NAFLD) or hepatocellular carcinoma (HCC), said method comprising administering to the subject a therapeutically effective amount of a medical agent comprising a polynucleotide, which medical agent is capable of silencing or knocking out the PKLR gene.

The embodiments of the first aspect as well as the discussion above apply to the second aspect mutatis mutandis.

The present disclosure provides, in a third aspect, a medical agent for use in a method of treatment of hepatocellular carcinoma (HCC), wherein the medical agent comprises a polynucleotide and is capable of silencing the PNPLA3 gene. The PNPLA3 gene has two protein coding transcripts (Transcript IDs ENST00000216180.7 and ENST00000423180.2).

As a fourth aspect of the present disclosure, there is provided a method of treating a subject having hepatocellular carcinoma (HCC), said method comprising administering to the subject a therapeutically effective amount of a medical agent comprising a polynucleotide, which medical agent is capable of silencing the PNPLA3 gene.

The present disclosure provides, in a fifth aspect, a medical agent for use in a method of treatment of hepatocellular carcinoma (HCC), wherein the medical agent comprises a polynucleotide and is capable of silencing the PCSK9 gene. The PCSK9 gene has one protein coding transcript (Transcript ID ENST00000302118.5).

As a sixth aspect of the present disclosure, there is provided a method of treating a subject having hepatocellular carcinoma (HCC), said method comprising administering to the subject a therapeutically effective amount of a medical agent comprising a polynucleotide, which medical agent is capable of silencing the PCSK9 gene.

The embodiments of aspects one and two as well as the discussion above apply to aspects three to six mutatis mutandis.

BRIEF DESCRIPTION OF THE FIGURES

The invention is now described, by way of example, with reference to the accompanying drawings, in which.

Figure 1:
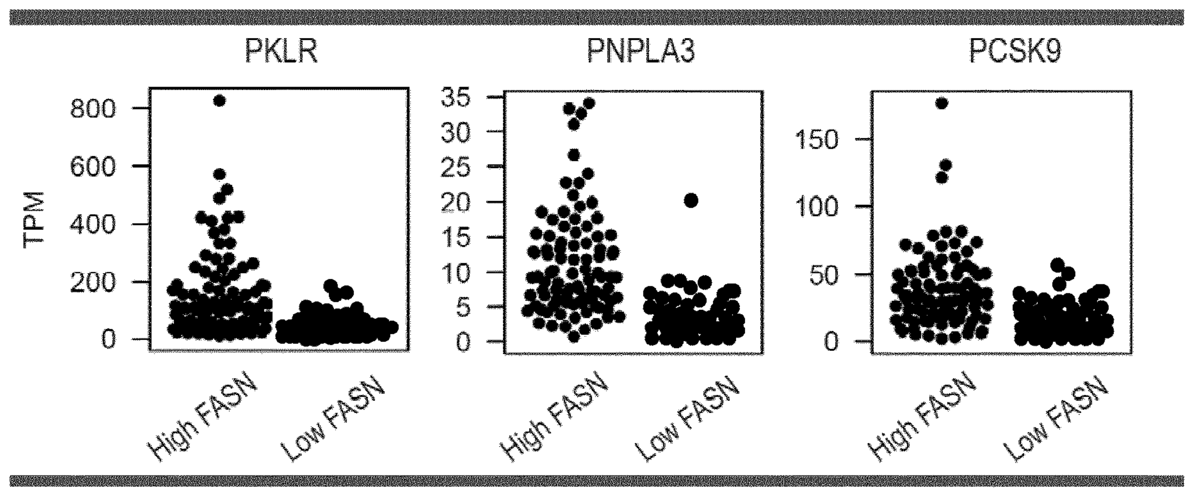
FIG. 1 shows expressions of PKLR, PNPLA3, and PCSK9 in HCC patients with high and low FASN expressions. Liver-specific genes were significantly (adjusted p-values<$1.0\times10^{-10}$) upregulated in patients high FASN expression compared to those with low FASN expression.

RNA was isolated for RT-PCR after interference for 24 hours; GAPDH was set as the internal reference. Cell counting was performed after interference for 72 hours. Data are presented as the means±standard errors of five independent experiments. Comparisons were performed by one-way ANOVA. Samples without any interference were assigned as controls. * represents a significant difference compared with the value in the control group (P<0.05).

FIG. 3: the relationship between the genes in mice and human samples. (A) TG content in the liver tissue of mice fed a zero-fat high sucrose diet (HSD) and chow diet (CD) for two weeks. The hepatic mRNA expressions of the Fasn, Pklr, Pcsk9, Pnpla3 and Hmgcr is measured in (B) mice fed a HSD and CD for two weeks, (C) Pcsk9 knockout and its littermates (WT) fed a CD for 10 weeks, (D) wild type HCC tumor and noncancerous samples, (E) $CB_1R$ knockout HCC tumor and noncancerous samples and (F) primary human hepatocytes treated with C75 for 4, 6, 8 and 24 h. Data are presented as the means±standard errors of independent experiments.

DETAILED DESCRIPTION

Rapid advances in omics technologies along with the adoption of large shared public databases has allowed for the generation and aggregation of massive sample data sets that can be used to construct comprehensive biological networks. These networks may provide a scaffold for the integration of omics data, thereby revealing the underlying molecular mechanisms involved in disease appearance and providing a better understanding of the variations in healthy and diseased tissue that may be used in the development of effective treatment strategies. In the study behind the present disclosure, tissue-specific CNs for 46 major human tissues and human liver cancer were generated and the tissue-specific functions were explored by using the topologies provided by these networks. An important aspect of a gene CN is modularity: genes that are highly interconnected within the network are usually involved in the same biological modules or pathways. The tissue-specific CNs were compared with the recently generated INs and it was found that physical interactions revealed meaningful functional relationships between genes. Next, using CNs, the emergent properties and behaviors of the affected genes in response to NAFLD and HCC were investigated at the system level rather than focusing on their individual functions and clinical utilities. The use of CNs also provided detailed information about the systems-level properties of such complex liver diseases.

Correlation analysis is used to identify co-expressions between different genes based on mRNA expression data. Although co-expression does not necessarily indicate a relationship among transcript levels, functional relationships between encoded protein coding genes are shown in the study behind the present disclosure. Co-expression analysis was applied to identify important alterations related to lipid metabolism, and promotion of cell survival and cell growth. In order to avoid possible false positives from co-expressed genes, a strict cut-off of Pearson's correlation coefficients was applied, but an advanced method to identify co-expressed genes for smaller number of false positives was developed. Here, correlations of gene expressions using normal tissue samples obtained from general population (i.e. GTEx) were calculated without selection bias. It was thus expected to identify general functional relationships, not only associated with a specific clinical indication. However, it is noteworthy that RNA-seq data generated for large and extensively-phenotyped cohorts improved the understanding of functional relationships between genes in a specific clinical indication.

Considering the increased prevelance of NAFLD in the worldwide as a hidden epidemic (Younossi et al, 2016), it is plausible to predict that NAFLD may become responsible for the future clinical and economical burden of HCC (Younossi et al, 2015). It has also been reported that HCC patients with NAFLD have poor outcome for disease progression (Younossi et al, 2015). Therefore it is relevant to identify common biological pathways and gene targets as driving forces in the pathologies for developing effective therapeutic modalities. In this context, system biology contributes to identification of novel targets that can be used in the development of efficient treatment strategies. A recent analysis described in (Mardinoglu et al, in preparation) and previous analysis (Mardinoglu et al, 2014a) indicated that DNL is a key pathway involved in the progression of the NAFLD. Previous analysis has also revealed DNL as one of the most tightly regulated pathways in HCC compared with noncancerous liver tissue (Björnson et al, 2015). FASN (rate-limiting enzyme in DNL) is believed to play key roles in NAFLD progression and development and HCC; therefore, inhibiting FASN may down-regulate the DNL, decrease the accumulated fat within the cells and decrease tumor growth. To improve the success rate of NAFLD and HCC treatment and to improve the survival prognosis of HCC patients, identification of non-toxic FASN inhibitors is of interest. To identify possible inhibitors, correlation analysis was applied to mRNA expression data derived from liver tissue with varying degree of fat and tumor samples. Co-expression analysis in these samples revealed that FASN is co-expressed with a number of genes that play roles in crucial biological processes involved fat accumulation and cancer cell metabolism.

The majority of publicly available liver tissue gene expression data were analyzed, correlation analysis was performed and ultimately co-expression networks for FASN were generated. Liver-specific gene targets, including PKLR, that can be inhibited for effective treatment of chronic liver diseases was identified. Finally, the predictions were validated by demonstrating the functional relationships among the expression of these genes and FASN, liver fat and cell growth, by using human cancer cell lines, mouse liver samples (4 different mouse studies) and human hepatocytes.

The present inventors make the following conclusions from the prior art:

- Wang et al. (Wang et al, 2002) have provided evidence that variants in the PKLR gene are associated with an increased risk of T2D, which has a pathogenesis similar to that of NAFLD.
- Ruscica et al. (Ruscica et al, 2016) have associated circulating PCSK9 levels with accumulated liver fat. In 201 consecutive patients biopsied for suspected NASH, liver damage has been quantified by NAFLD activity score, circulating PCSK9 by ELISA, and hepatic mRNA by qRT-PCR in 76 of the patients. Circulating PCSK9 has been found to be significantly associated with hepatic steatosis grade, necroinflammation, ballooning, and fibrosis stage (Ruscica et al, 2016). Circulating PCSK9 has also been found to be significantly associated with hepatic expression of SREBP-1c and FASN, whereas PCSK9 mRNA levels have been found to be significantly correlated with steatosis severity and hepatic APOB, SREBP-1c and FASN expression (Ruscica et al, 2016).
- Aragones et al. (Aragones et al, 2016) have evaluated the association between liver PNPLA3 expression, key genes in lipid metabolism, and the presence of NAFLD in morbidly obese women and have reported that PNPLA3 expression was related to HS in these subjects. Their analysis indicates that PNPLA3 may be related to lipid accumulation in the liver, mainly in the development and progression of simple steatosis.

PNPLA3 was also emphasized as a genetic determinant of risk factor for the severity of NAFLD (Salameh et al, 2016). Furthermore, higher prevelance for HCC development and poorer prognosis was reported to be associated with PNPLA3 polymorphism in viral and non-viral chronic liver diseases (Khlaiphuengsin et al, 2015). A potential unifying factor upstream of these genes is the cannabinoid-1 receptor, stimulation of which was found to upregulate several of the above listed target proteins, including Fasn, Pklr, Pnpla3 and Pcsk9 in mouse models of obesity/metabolic syndrome and HCC, as documented and detailed.

Moreover, it was found in the study behind the present disclosure that a number of genes, e.g ACACA, were significantly co-expressed with FASN. It has been suggested that inhibition of ACACA may be useful in treating a variety of metabolic disorders, including metabolic syndrome, type 2 diabetes mellitus, and fatty liver disease (Harriman et al, 2016). However, the present inventors' analysis indicate that potential inhibition of ACACA may have severe side effects in other human tissues as the inhibitors of FASN.

In conclusion, the present disclosure demonstrates a strategy whereby tissue-specific CNs are used to identify deregulations of biological functions in response to disease and reveals the effects on relevant expression of genes in liver. Eventually, a liver-specific drug target that can be silenced for treatment of liver diseases including NAFLD and HCC has been identified.

Further, a systems level analysis have been performed to predict the global effect of the inhibition and over expression of liver-specific genes including PKLR, PNPLA3 and PCSK9. The analysis confirmed that these genes are targets for NAFLD and HCC treatment since their perturbations are also linked to key biological functions related to lipid metabolism and cell proliferation. The analysis was mainly focused on the modulation of PKLR. PKLR converts PEP to pyruvate, which is the main carbon source, and its perturbation may significantly affect the pyruvate levels and PEP/pyruvate ratio in cell. The PEP/pyruvate ratio may also act as a metabolic signal that control the expression of mitochondria genes via some regulatory pathway, (i.e. hypoxia response), since the expression of HIF1A and PDK are both significantly negatively correlated with PKLR.

PKLR exhibited the strongest correlation with the expression of FASN and a significant correlation with the genes involved in pathways related to lipid metabolism based on our transcriptomic analysis. The analysis also indicated that inhibition of PKLR decrease total triglyceride level as well as cell growth.

The differentially expressed genes (DEGs) in both inhibition and overexpression of PKLR are significantly enriched in the mitochondrial metabolic functions and genes localized in mitochondria. This implicated a potential regulatory role of PKLR in maintaining mitochondrial functions. KEGG pathway analysis also revealed that DEGs with PKLR perturbation are enriched in pathways related to lipid metabolism involved in steroid biosynthesis, PPAR signaling pathway, fatty acid degradation and synthesis as well as cancer development including DNA replication, cell cycle, and p53 signaling. These results indicate that PKLR might exert persistent effects on the whole disease progression from steatosis to liver malignance in consistence with the findings based on human tissue transcriptomics and proteomics data that are discussed above.

In line with phenotypic data from cell experiment, differential expression analysis revealed close relationship between PKLR and genes cluster enriched in pathway that involved in cell proliferation. Of note, most of genes involved in DNA replication (in eukaryotes) were highly co-expressed with the genes affected with PKLR perturbation (25 of 32 genes (78%) presented with significant tendency). Moreover, TP53, a driver gene involved in precancerous DNA replicative stress was also significant differentially expressed after perturbation of PKLR. As a response to DNA damage, increased replicative stress may induce genomic instability and finally cause cancer development. In addition, some key drivers e.g. over-production of reactive oxygen species (ROS) may also accelerate this process. The results presented herein support that PKLR act as an oncogene by inducing severer replicative stress as hallmark of cancer development.

Coordinated expression changes by modulating liver-specific genes at the genome-scale level was observed and corresponding regulatory modules of given target genes was identified. Transcriptomic data together with network analysis elucidated not only biological processes perturbed by specific target gene, but also global reprogramming of gene expressions by identifying key transcription factors (TFs).

In conclusion, the global effect of inhibiting or overexpressing liver-specific gene targets including PKLR, PNPLA3, and PCSK9, in HepG2 cells was revealed based on transcriptome data and HepG2-specific IN analysis. It was observed that modulation of PKLR effect the total fat content and cell viability indicating that PKLR can be targeted for development of efficient treatment strategies for both NAFLD and HCC.

EXPERIMENTAL SECTION

First Procedures

Tissue-Specific CNs

RNA-seq data from human tissues were downloaded from the GTEx database, and their reads per kilobase per million (RPKM) values were transformed into transcripts per kilobase per million (TPM) values. From each RNA-seq dataset, one-third of the genes with the lowest expression levels were excluded from calculating Pearson's correlation coefficients of gene expression and the highest correlated gene pairs were combined into a respective tissue CN.

On the basis of the network connectivity of each tissue CN, co-expressed genes were clustered by using the modularity-based random walk method from the cluster walktrap function of the igraph package in R (Pons & Latapy, 2005). Among those gene groups, the half of the highest connected groups were selected as key co-expression clusters on the basis of their clustering coefficients. A liver CN was produced with those co-expression clusters as nodes and their significant connections by edges. For example, the edges of two co-expression clusters, A and B, were identified if their observed connections ($O_{AB}$) were twice as high as the expected connections ($E_{AB}$). Expected connections were defined by the normalized sum of multiplications of the degree of connectivity of genes in two clusters (i.e., $E_{AB}=\Sigma k_a \times k_b/2N$; a ∈□A, b ∈, N=all nodes in the network). Next, genes belonging to key co-expression clusters were collected in each tissue and it was tested whether they were enriched in biological process GO terms in MSigDB (Subramanian et al, 2005) by using hypergeometric tests.

Comparing Physical Networks with CNs

RNs and PPINs of liver, skeletal muscle and adipose tissues from prior published data (Lee et al, 2016) were used as sources of physical interaction network data. Co-regulated gene pairs from the physical interactions were identified by selecting genes sharing TF binding (from RNs) or genes sharing protein interactions (from PPINs). On the basis of the number of co-bound TFs or co-interacting proteins, called co-regulators, the highest co-regulated gene pairs (i.e., gene pairs with the highest numbers of co-bound TFs or co-interacting proteins (top 0.1%)) and gene pairs with no co-regulation were selected. Using Pearson's correlation coefficients of the gene expression level of each tissue from GTEx, the mean Pearson's correlation coefficients of gene pairs of interest, such as physically linked gene pairs or co-regulated gene pairs were calculated. The edges of physical networks or their co-regulatory networks were randomly permutated among genes in respective actual networks by 1000×, and their mean correlation coefficients were compared with those from original networks. TFs or proteins highly co-expressed with respective bound genes were also identified by comparing the co-expression levels of given gene pairs to overall levels. TFs or proteins were selected if co-expression levels of given linked gene pairs were higher than the overall levels by using Kolmogorov-Smirnov (KS) tests (P-value<0.05) and absolute values of mean Pearson's correlation coefficients (>0.1). Finally, mean co-expression levels of co-regulated gene pairs were examined according to their number of co-regulators. Co-regulated gene pairs exceeding the cut-off were selected and mean Pearson's correlation coefficients of the corresponding gene pairs were calculated.

Finding the Most Influential TFs for Co-Expression on the Basis of Variable Importance Score For liver tissue, a feature matrix between the most highly co-expressed gene pairs (top 1%) and their co-bound TFs was constructed. In this matrix, a value of one was assigned for given co-expressed gene pairs that were co-bound by TFs and a value of zero was otherwise assigned. For each co-expressed gene pair, co-bound TFs were considered as predictor variables and the co-expression value as the response variable and they were fitted to the Random Forest model. From the model, variable importance scores of all TFs were calculated and used as a metric to show the most influential TFs for co-expression.

Identifying Liver-Specific Reaction Clusters on the Basis of Tissue Co-Expression of Enzymes From the HMR2 database, human metabolic reactions with known enzymes were collected. Between the two reactions, Pearson's correlation coefficients of enzyme gene expression in liver tissue were calculated, and if there were multiple enzymes for a single reaction, the maximum value among possible co-expressions was taken. On the basis of co-expression values among metabolic reactions, hierarchical clustering was performed and reactions were classified into 100 clusters for liver tissue. To compare the co-expression values of metabolic reactions in different tissues and tumor tissue, the co-expression values in not only liver tissue but also adipose subcutaneous, skeletal muscle and HCC tumor tissues were calculated. Subsequently, the differences in mean co-expression values of given reaction clusters between liver tissue and other tissues were identified after transforming co-expression values into Fisher Z-values. On the basis of differential Fisher Z-values, the top 1% of reaction clusters of the highest in each comparison (adipose or muscle tissues) were identified as liver-specific reaction clusters. Likewise, an HCC de-regulated reaction cluster was identified on the basis of differential Fisher Z-values (top 1%).

Finally, using liver RN, TFs highly bound at genes encoding enzymes in given liver reaction clusters were examined and TFs whose binding was significantly enriched in given clusters were identified by hypergeometric tests. From those enriched TFs, reaction clusters in which the enriched TFs had higher variable importance scores than overall scores according to KS tests (P<0.25) were selected and denoted as highly regulated reaction clusters in liver tissue.

FASN Co-Expressed Genes in Human Tissues and HCC Tumors

In each normal tissue (GTEx) or HCC tumor tissue (TCGA), Pearson's correlation coefficients of gene expression between FASN and other protein-coding genes expressing more than 1 TPM were calculated and the top 100 most-correlated genes were selected. In addition, correlations of log-transformed expression values in HCC tumors were calculated. To select tissue-specific genes, the top 100 most correlated genes to FASN in HCC tumor tissue by the RNA tissue category in the Human Protein Atlas (ver. 16) were examined; in particular, genes "tissue-enhanced" or "tissue-enriched" in liver tissue were selected. Those genes with tissues that were most correlated were also examined and genes that were present in fewer than three human tissues were selected.

Differential Expression Analysis of HCC Patients Stratified Based on FASN Expressions Using raw count data from HCC patients, patients were stratified into two groups; patients having FASN expression above the upper quartile and patients having FASN expression under the lower quartile. Between the two groups, differentially expressed genes were examined by negative binomial test using DESeq (Anders & Huber, 2010).

Cell Line Experiments

For subsequent experiments, K562 and HepG2, human immortalized myelogenous leukemia and hepatic cell lines, respectively, were selected. Both cell lines were cultured in RPMI-1640 medium (R2405, Sigma-Aldrich) supplemented with 10% fetal bovine serum (FBS, F2442, Sigma Aldrich) and incubated in 5% $CO_2$ humidity at 37° C.

To confirm the speculated CN, chemical inhibitors and RNA interference (RNAi) assays were chosen to interfere with the immortalized cell lines (including K562 and HepG2) and the subsequent candidate gene expression and cell growth patterns were observed. More specifically, the experimental protocol was as follows: (1) C75 (C5490, Sigma-Aldrich), as a well-known fatty acid synthase [FAS] inhibitor, was added to cells at 80% confluence with a final concentration of 20, 40, 60, or 80 μM (taking cells without C75 interference as the control); (2) cells at 80% confluence were separately transfected with three pairs of Silencer® pre-designed PKLR-targeted siRNAs (clone ID: 53 (SEQ ID NO:2 and SEQ ID NO:3), 54 (SEQ ID NO:2 and SEQ ID NO:5), Life Technologies) at 15 nM by using Lipofectamine® RNAiMAX (13778075, Life Technologies). Cells incubated in medium with non-target negative control siRNA at 15 nM (4390843, Life Technologies) were assigned as the control.

Total RNA was isolated with TRIzol reagent (15596026, Thermo Fisher Scientific) after treatment with C75 or siRNA for 24 hours. The expression profiles of key genes (FASN, PKLR in K562/HepG2, and PNPLA3, PCSK9 only in HepG2 cells) in the co-expression network were measured and analyzed via quantitative real-time PCR with iTaq Universal SYBR Green One-Step Kit (1725151, Bio-Rad), using anchored oligo (dT) primer based on CFX96™ detection system (Bio-Rad). GAPDH was set as the internal control for normalization. The primer sequences were SEQ ID NO:9 (FASN forward), SEQ ID NO:10 (FASN reverse), SEQ ID NO:11 (PKLR forward), SEQ ID NO:12 (PKLR reverse), SEQ ID NO:13 (PNPLA3 forward), SEQ ID NO:14 (PNPLA3 reverse), SEQ ID NO:15 (PCSK9 forward), SEQ ID NO:16 (PCSK9 reverse), SEQ ID NO:17 (GAPDH forward) and SEQ ID NO:18 (GAPDH reverse). Variation in cell proliferation was detected with a Cell Counting Kit-8 (CCK-8, CK04, Dojindo) after interference by C75/siRNA for 72 hours. All experiments were performed strictly according to the manufacturer's instructions and were repeated at least in triplicate for three samples and yielded similar results.

Mouse Experiments

Twenty male C57BL/6N mice were fed a standard mouse chow diet (Purina 7012, Harlan Teklad) and housed under a 12-h light-dark cycle. From 8 weeks of age, the mice were fed either a HSD diet (TD.88137, Harlan Laboratories, WI, USA) or CD for two weeks. The mice were housed at the University of Gothenburg animal facility (Lab of Exp Biomed) and supervised by university veterinarians and professional staff. The health status of the mice was constantly monitored according rules established by the Federation of European Laboratory Animal Science Associations. The experiments were approved by the Gothenburg Ethical Committee on Animal Experiments.

In liver cancer mouse model, 25 mg/kg of DEN (Sigma) were injected to $CB_1R^{+/+}$ and $CB_1R^{-/-}$ littermates in C57BL/6J background two weeks after birth, the presence of the HCC tumor was verified and its size was measured with magnetic resonance imaging (MRI) eight months after the DEN administration (Mukhopadhyay et al, 2015). It has been observed that activation of hepatic $CB_1R$ promoted the initiation and progression of chemically induced HCC in mice (Mukhopadhyay et al, 2015). Total RNA was isolated from tumor area and noncancerous area of liver tissue samples obtained from six DEN-treated (HCC) $CB_1R^{+/+}$ and six $CB_1R^{-/-}$ mice (Mukhopadhyay et al, 2015). rRNA-depleted RNA, 100 ng for each sample, was treated with RNase III to generate 100- to 200-nt fragments, which were pooled and processed for RNA sequencing. All data were normalized based on housekeeping genes used by Program CLC Genomics Workbench program (version 5.1, CLC Bio, Boston, USA). These absolute numbers were extracted from the reads and the data were adjusted to non-HCC biopsies for each gene.

Human Hepatocytes

Human primary hepatocytes were purchased from Biopredic International. Twenty-four hours after arrival (48 hours after isolation), human hepatocytes were treated with 40 μg/ml of C75 or dimethyl sulfoxide (DMSO) for 4, 6, 8 or 24 hours.

mRNA Expression in Mouse Liver and Human Primary Hepatocytes

Total RNA was isolated from human hepatocytes and snap-frozen mouse liver with an RNeasy Mini Kit (Qiagen). cDNA was synthesized with a high-capacity cDNA Reverse Transcription Kit (Applied Biosystems) and random primers. The mRNA expression levels of genes of interest were analyzed via TaqMan real-time PCR in a ViiATM7 System (Applied Biosystems). The TaqMan Gene Expression assays used were Mm01263610_m1 (for mouse Pcsk9), Mm00662319_m1 (mouse Fasn), Mm00443090_m1 (mouse Pklr), Mm00504420_m1 (mouse Pnpla3), Mm01282499_m1 (mouse Hmgcr), Hs00545399_m1 (human PCSK9), Hs01005622_m1 (human FASN), Hs00176075_m1 (human PKLR), Hs00228747_m1 (human PNPLA3), and Hs00168352_m1 (human HMGCR) (all from Applied Biosystems). Hprt (mouse Mm03024075_m1) and GADPH (human Hs02758991_g1) (Applied Biosystems) were used as internal controls.

First Results

Generation of CNs for Human Tissues

A common observation in gene expression analysis performed for different clinical conditions is that many genes known to be functionally related often show similar expression patterns, thus potentially indicating shared biological functions under common regulatory control. Thus, identifying co-expression patterns instead of only differential expression patterns may be informative for understanding altered biological functions. To identify genes with similar gene expression profiles, RNA-seq data comprising 51 tissues, including liver, muscle, subcutaneous and omental adipose, along with other major human tissue samples were retrieved from the Genotype-Tissue Expression (GTEx) database (GTEx, 2013). To measure the tendency of gene expression correlation, the Pearson correlation coefficients (r) between all gene pairs in 46 human tissues with more than 50 samples were calculated and all genes were ranked according to the calculated r. The top 1% correlation value of each tissue was used as a cut-off indicating that two genes were co-expressed (average r=0.576 for 46 tissues) and therefore had the same number of co-expression links for all tissues, thus yielding 1,498,790 links, and they were combined to construct the tissue-specific CNs. The resulting CNs were as follows: liver tissue contained 11,580 co-expressed genes, muscle tissue contained 10,728 co-expressed genes and subcutaneous and omental adipose tissue contained 12,120 and 11,117 co-expressed genes.

Given the connectivity of tissue-specific co-expression links, groups of highly co-expressed genes, termed co-expression clusters, were found by using the random walk community detection algorithm (Pons & Latapy, 2005). Among these clusters, the most highly co-expressed key clusters were selected on the basis of their clustering coefficients (average clustering coefficient=0.522). It was found that genes associated with key co-expression clusters in tissues significantly overlapped with tissue-specific genes presented in the Human Protein Atlas (HPA) (Uhlen et al, 2015), when global proteomics and transcriptomics data were available for more than 30 human tissues. Analysis indicated that 75.6% of 41 HPA-matched tissues had key co-expression clusters significantly enriched in tissue-specific genes (hypergeometric test $P<0.01$), thus suggesting the tissue-specific roles of the genes associated with the key clusters.

To investigate tissue-specific functions of the genes associated with the key co-expression clusters, gene ontology (GO) enrichment analysis was performed by using the GO biological processes (BP) terms in MSigDB (Subramanian et al, 2005) (hypergeometric test $P<1.0\times10^{-4}$). For example, in liver tissue, it was found that genes associated with key co-expression clusters were enriched in terms comprising the immune response, hemopoiesis and fatty acid metabolic processes, whereas in testis tissue, co-expression clusters were enriched in cell cycle, metabolism, and reproduction. Likewise, the enrichment of the genes associated with key co-expression clusters in other metabolically active tissues, including skeletal muscle and subcutaneous and omental adipose tissues, compared with the significantly enriched GO BP terms in liver tissue was investigated, and it was found that the GO BP term "hemopoiesis" was enriched only in liver tissue, whereas "muscle development" was enriched only in skeletal muscle. In both subcutaneous adipose tissue and liver tissue, genes associated with the key clusters were significantly enriched in fatty acid metabolic processes.

Hence, the analysis indicated that genes involved in fatty acid metabolism are significantly co-expressed in liver and adipose tissues.

Increased Co-Regulation Results in Increased Co-Expression

INs for metabolic tissues, including liver, muscle and adipose tissues have previously been presented, and the physical links between TFs and target proteins and enzymes (Lee et al, 2016) have been identified. Here, the overlap between the INs and CNs was investigated and the potential deregulation of metabolism in metabolically active human tissues was analyzed by using the topology on the basis of the regulatory interactions and protein-protein interactions of INs by comparing the mean co-expression of actual networks with that of networks randomly permutated by 1,000 repetitions. It was found that most of the actual tissue regulatory networks (RNs) and PPINs showed higher co-expression than randomly permutated networks in liver and other metabolic tissues. It was also observed that regulatory interactions built from in vitro differentiated adipocytes (Lee et al, 2016) had less specificity than co-expression calculated by using subcutaneous adipose tissue RNA-seq data demonstrating higher tissue specificity.

Target proteins regulated by the same TFs or interacting with the same proteins may have similar gene expression patterns (Zhang et al, 2016). Hence, the co-expression of co-regulated gene pairs in RNs were examined and it was found that their mean co-expression was higher in actual RNs than in randomly permutated RNs in the liver and other metabolic tissues. Moreover, the co-expression of gene pairs that were not regulated by the same TFs were examined and it was found that their mean co-expression was lower in actual liver RNs than in randomly permutated RNs in liver tissue and other metabolic tissues. Similarly, the co-expression of co-interacting gene pairs for the same proteins in PPINs was examined and relatively lower mean co-expression was found in actual liver PPINs than in randomly permutated PPINs in liver tissue and other metabolic tissues, as compared with the mean co-expression of the actual RNs. It was also found that mean co-expression in PPINs was lower in actual PPINs than in randomly permutated PPINs in liver tissue and other metabolic tissues when proteins that did not interact with the same proteins were compared. The analysis indicated that physical interactions defined by the RNs and PPINs can be used to explain protein co-expression. Moreover, it was observed that the two target proteins regulated by the same TFs may have similar expression patterns, whereas two target proteins interacting with the same protein may have less similar expression patterns.

Target proteins may be regulated by more than one TF in RNs, thus potentially affecting their expression patterns. In this context, the co-expression of two target proteins regulated by the same TFs was determined and it was found that an increased number of co-bound TFs were likely to be associated with increased mean co-expression levels in liver, skeletal muscle and adipose tissue. Also, a similar analysis in PPINs on the basis of the two target proteins that co-interacted with the same proteins was repeated and it was found that the increased number of co-interacting proteins was not directly proportional to increased mean co-expression although the mean co-expression levels were high in the liver and other tissues analyzed. Analysis indicates that protein interactions provide evidence for increased co-expression by RNs compared with PPINs in metabolic tissues.

The TFs and proteins that were highly co-expressed with their target genes or proteins in RNs and PPINs, respectively, ($|r|>0.1$ and Kolmogorov_Smirnov (KS) two-sided test, $P<0.05$) were also identified. The biological functions associated with these TFs and proteins using DAVID (Huang et al, 2009) were investigated and it was found that the TFs in liver RN were enriched in the regulation of transcription and cell differentiation (false discovery rate [FDR]<0.01) and that the proteins in liver PPIN were enriched in RNA splicing (FDR<0.01), which is involved in post-transcriptional regulation. To identify the most influential TFs in the co-expression of gene pairs, the most highly co-expressed gene pairs (top 1%) were used, the co-binding matrix of bound TFs was established on the basis of RNs and the variable importance score was calculated by using the Random Forest model in the liver. Among the top 1% most influential TFs (76 TFs), e.g., YY1, CTCF, RAD21, SREBF1 and SREBF2, TFs enriched in liver development, interphase of the mitotic cell cycle and response to lipids (FDR<0.001) were found, thus suggesting that many influential TFs are involved in liver-specific functions.

Highly Co-Expressed Metabolic Pathways in the Liver

On the basis of physical and functional links provided by the networks, it was examined which metabolic pathways are regulated specifically in the liver. The group of metabolic reactions catalyzed by highly co-expressed enzymes in liver tissue were first identified by using the Human Metabolic Reaction database (HMR2) (Mardinoglu et al, 2014a). Taking the maximal co-expression of enzymes between two metabolic reactions, a reaction co-expression matrix among all reactions was established. From this matrix, hundreds of clusters of reactions with highly co-expressed enzymes by using hierarchical clustering were identified. By comparing their co-expression in liver tissue with the co-expression in adipose subcutaneous and skeletal muscle tissues, metabolic reaction clusters that were co-expressed only in liver tissue were identified. On the basis of Fisher Z-transformed differences in tissue co-expression, ten reaction clusters of the most differential co-expression levels between liver and muscle tissue or between liver and adipose tissue were identified; four reaction clusters overlapped in both cases.

Among those clusters, the TFs that were highly co-bound with enzymes of those reaction clusters were determined by using the hypergeometric test ($P<0.05$) and it was found that each reaction cluster was governed by different sets of TFs. For example, metabolic nuclear receptors, such as the farnesoid X receptor (FXR or NR1H4), pregnane X receptor (PXR or NR1I2) and RXRB, were highly co-bound with enzymes catalyzing the reaction in cluster 14, whereas SREBF2, a regulator of lipid homeostasis, was highly co-bound with enzymes catalyzing reactions in cluster 9. These findings indicated that enzymes catalyzing reactions in clusters 14 and 9 would share regulatory controls in response to metabolic alterations. Next, it was determined which reaction clusters were enriched in influential TFs that had been identified. Using variable importance scores of TFs, it was determined whether highly co-bound TFs of reaction clusters had variable importance scores higher than the overall scores (KS one-sided test, $P<0.25$). It was found that reaction clusters including 9, 14, 40 and 58 had significantly enriched TFs with highly variable importance scores, thus providing strong evidence of liver-specific regulation from physical and co-expression links. Through metabolic subsystem annotation from HMR2, it was observed that reaction cluster 9 was enriched in mitochondrial transport, pyruvate metabolism and lipid metabolism, cluster 14 was enriched in fatty acid synthesis, cluster 40 was enriched in cholesterol metabolism, and cluster 58 was enriched in amino acid metabolism (hypergeometric test $P<0.01$); these results indicated reactions involved in pathways that are regulated in only the liver and are primarily associated with lipid metabolism.

Next, it was determined which liver reaction clusters were deregulated in HCC, on the basis of co-expression of those clusters in HCC tumor tissue from The Cancer Genome Atlas (TCGA). First RNA-seq data for 371 HCC tumors from TCGA were retrieved and Pearson's correlation coefficients between the gene pairs were calculated. As liver-specific co-expression clusters were identified, ten reaction clusters that were deregulated in HCC tumors were identified on the basis of Fisher Z-transformed differences in co-expression between GTEx liver data and TCGA HCC data. Among those deregulated clusters, five reaction clusters were identified as liver-specific clusters as opposed to adipose and/or muscle tissue clusters: reaction clusters 9, 14, 56, 62 and 65. Of note, reaction clusters 9 and 14 were identified on the basis of their regulation with strong evidence regarding co-expression and physical clues. In HCC, deregulation of these liver-specific reaction clusters primarily associated with fatty acid synthesis may be linked to HCC pathogenesis.

Identification of Liver-Specific FASN Inhibitors for the Treatment of NAFLD and HCC The expression of fatty acid synthase (FASN), which catalyzes the last step in de novo lipogenesis (DNL), is significantly upregulated in NAFLD (Dorn et al, 2010) and HCC (Björnson et al, 2015). It has recently been shown that short-term intervention with an isocaloric carbohydrate-restricted diet causes a large decrease in liver fat accompanied by striking rapid metabolic improvements (Mardinoglu et al, in preparation). Clinical characteristics, body composition, liver fat, hepatic DNL and hepatic β-oxidation were measured and it was found that the diet caused rapid and significant sustained decreases in liver fat, DNL, plasma triglycerides and very-low-density lipoprotein triglycerides and a parallel increase in β-hydroxybutyrate, an indicator of increased hepatic β-oxidation. Hence, DNL may be targeted for the development of effective treatment strategies for NAFLD and other chronic liver diseases, e.g., HCC.

However, small-molecule FASN inhibitors (e.g., C75, cerulenin) suffer from pharmacological limitations that prevent their development as systemic drugs (Pandey et al, 2012). These side effects can also be explained by the high expression of FASN in almost all major human tissues (Uhlen et al, 2015; Uhlen et al, 2016). Thus, it was hypothesized that the identification of liver-specific FASN inhibitors might allow for the development of effective treatment strategies for NAFLD and HCC. Highly co-expressed genes with FASN were identified on the basis of CNs generated using GTEx and TCGA data, which have been used as representative datasets for NAFLD and HCC, respectively. CN analysis allowed the identification of genes functionally related to FASN in liver and other major human tissues.

Using DAVID, it was found that the top 100 genes co-expressed with FASN in liver CN were significantly enriched in GO BP terms, including carboxylic acid, oxoacid, hexose, monosaccharide, acyl-CoA and fatty acid metabolic processes, protein transport, secretion, regulation of secretion, and negative regulation of cell communication (Huang et al, 2009). Also, the top 100 co-expressed genes with FASN in liver CN were compared with the genes in 45 other tissue CNs and pyruvate kinase liver and red blood cell (PKLR), an enzyme phosphorylating pyruvate from glycolysis to the TCA (citric acid) cycle and also in fatty acid synthesis, was identified. PKLR was found to be a liver-specific gene that is co-expressed with FASN.

In HCC CN, it was found that the top 100 genes co-expressed with FASN were significantly enriched in GO BP terms, including animal organ development, carboxylic acid, oxoacid, cholesterol, secondary alcohol, sterol and fatty acid metabolic processes, along with steroid, sterol and alcohol biosynthetic processes. ELOVL6, ACACA and SCD, involved in fatty acid biosynthesis, were found to be the top genes co-expressed with FASN in HCC CN. In addition, Pearson's correlations from log-transformed gene expressions in HCC were calculated in order to check for robustly co-expressed genes. It was found that 40 of the genes in top-100 co-expressed genes were significantly co-expressed with FASN before and after log-transformation. Those robustly co-expressed genes with FASN in HCC CN were compared with the top 100 co-expressed genes in CNs of 46 human tissues and PKLR, patatin-like phospholipase domain containing 3 (PNPLA3) and proprotein convertase subtilisin/kexin type 9 (PCSK9), referred as liver-specific genes, were found to be the only genes co-expressed with FASN in less than three human tissues.

Next, the global gene expression profiling of the HCC tumors in the upper quartile with highest expression of FASN (n=93) was compared with the lower quartile of HCC tumors (n=93) with the lowest expression of FASN using DESeq package (Anders & Huber, 2010) to analyze the expression profile of liver-specific genes its key role in cancer progression. It was found that the expression of PKLR, PNPLA3, and PCSK9 was significantly increased in patients with high FASN expression compared to those with low FASN expression (FIG. 1).

The expression patterns of PKLR, PNPLA3, and PCSK9 in the Human Protein Atlas, in which the expression of all human protein coding genes have been measured in 32 major human tissues, were determined, and these genes were identified as liver-specific genes (Kampf et al, 2014; Uhlen et al, 2015). Hence, the liver-specific gene PKLR is a candidate target for the treatment of HCC and NAFLD. Further, the liver-specific genes PNPLA3 and PCSK9 may potentially be targeted for the treatment of HCC. Due to the direct involvement of PKLR, PNPLA3 and PCSK9 in lipid metabolism, the relationship between FASN and these three liver-specific genes was the focus of the rest of the studies.

Validation of Physical Interactions by Using Human Cancer Cell Lines

It was hypothesized that inhibition of liver-specific targets that are co-expressed with FASN would inhibit FASN expression and decrease fat synthesis. This inhibition would also inhibit tumor growth in the case of HCC, because fatty acids play key roles in HCC progression and development. To validate the hypothesis and to demonstrate the physical interactions between FASN and liver-specific genes, the cell lines with the highest PKLR mRNA expression levels were first screened by using the data generated in the Human Protein Atlas (Uhlen et al, 2015). The K562 leukemia cell line was identified as having the highest PKLR expression using recently published data in Cell Atlas (Thul et al, 2017). The cell line was treated with C75, a FASN inhibitor, at different concentrations for 24 hours. The purpose of this experiment was to test whether FASN inhibition may affect the co-expressed genes with FASN (i.e. PKLR).

Figure 2A:
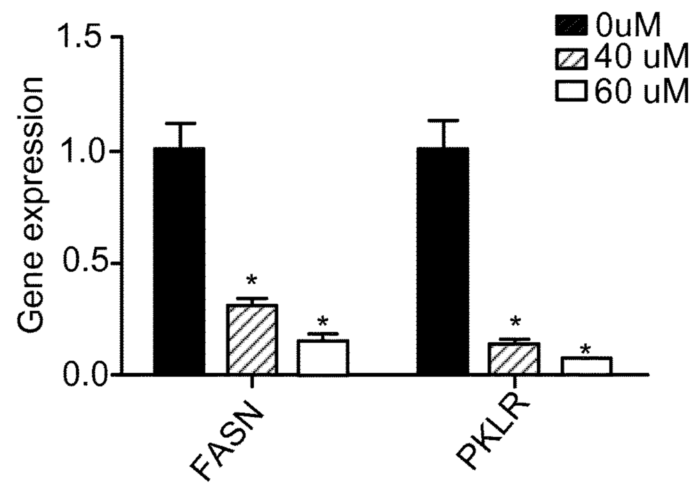
FIG. 2: gene expression and proliferation of K562 and HepG2 cells after interference by C75 and PKLR-specific siRNA. (A) FASN and PKLR expression levels in K562 cells after interference by different doses (0, 40, and 60 μM) of C75. (B) Cell growth in K562 cells after interference by different doses (0, 20, 40, 60, and 80 μM) of C75. (C) FASN, PKLR, PNPLA3 and PCSK9 expression levels in HepG2 cells after interference by different doses (0, 40, and 60 μM) of C75. (D) Cell growth in HepG2 cells after interference by different doses (0, 20, 40, 60, and 80 μM) of C75. (E) FASN and PKLR expression levels in K562 cells after interference by PKLR-specific siRNA (siRNA 53, siRNA 54). (F) Cell growth in K562 cells after interference by PKLR-specific siRNA (siRNA 53, siRNA 54). (G) FASN, PKLR, PNPLA3 and PCSK9 expression levels in HepG2 cells after interference by PKLR-specific siRNA (siRNA 53, siRNA 54). (H) Cell growth in HepG2 cells after interference by PKLR-specific siRNA (siRNA 53, siRNA 54).
Figure 2B:
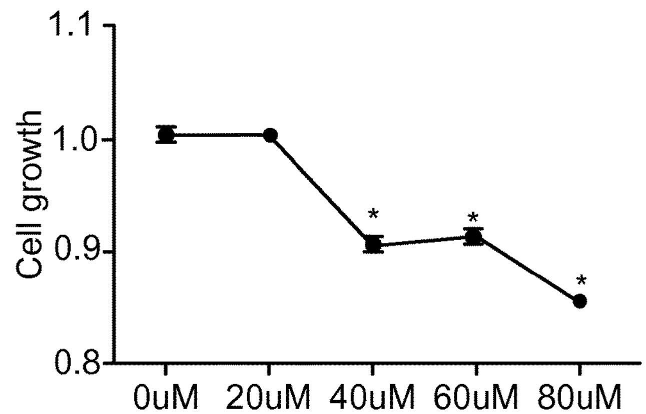
Figure 2C:
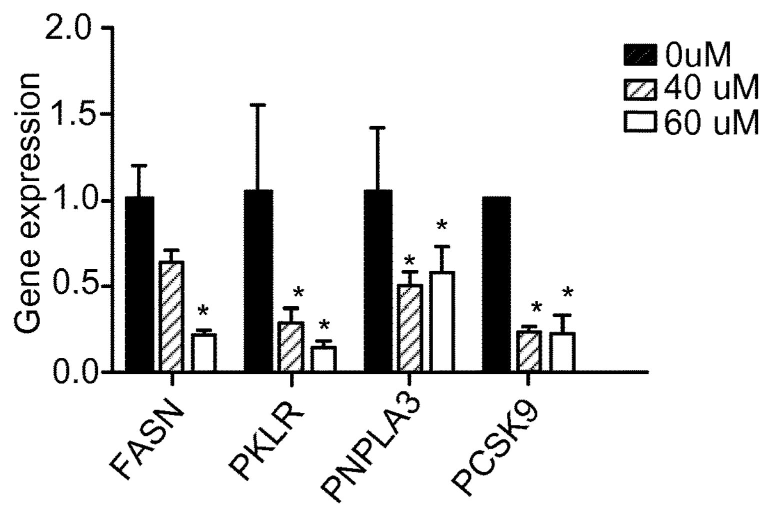
Figure 2D:
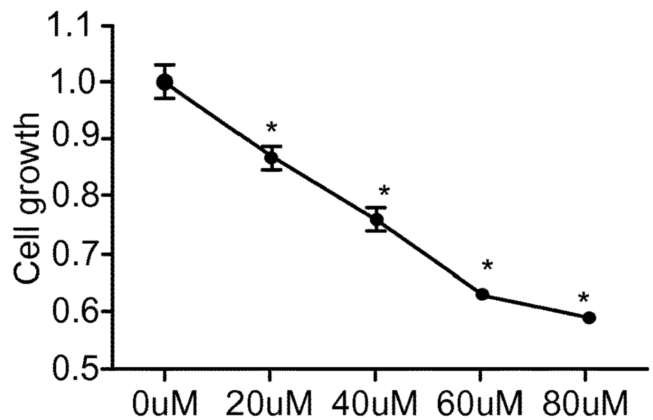

It was found that FASN and PKLR expression levels were significantly decreased (FIG. 2A). Moreover, it was determined that decreased FASN and PKLR expression resulted in a significant decrease in cell growth (FIG. 2B). Next, the HepG2 human cancer cell line was treated with C75 and it was found that FASN expression and the expression levels of liver-specific genes, including PKLR, PNPLA3 and PCSK9, were significantly decreased after 24 hours (FIG. 2C). Similarly, it was found that the growth of HepG2 cells was significantly decreased after treatment of the cells with different concentrations of C75 (FIG. 2D).

Figure 2E:
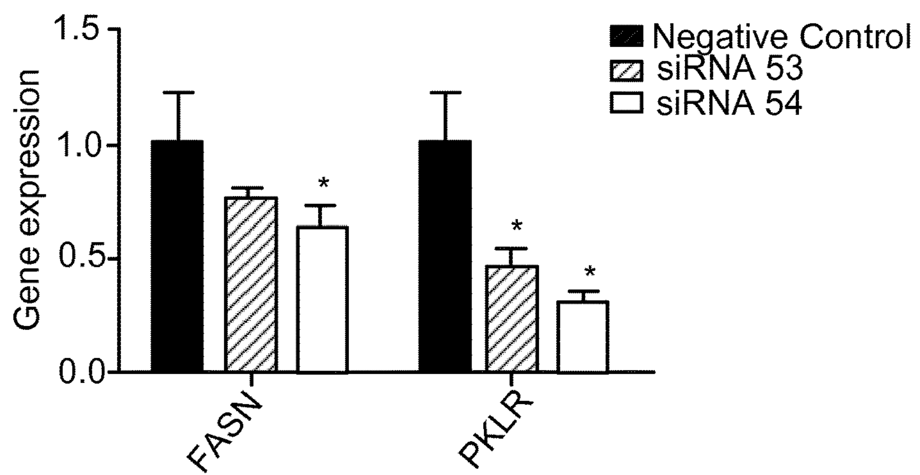
Figure 2F:
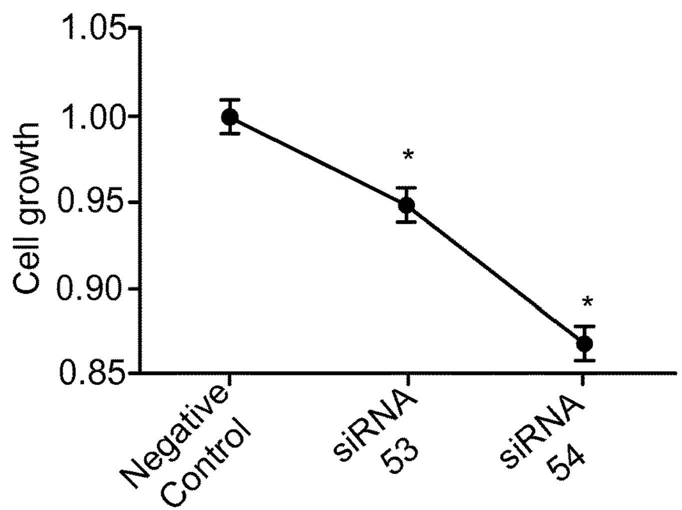
Figure 2G:
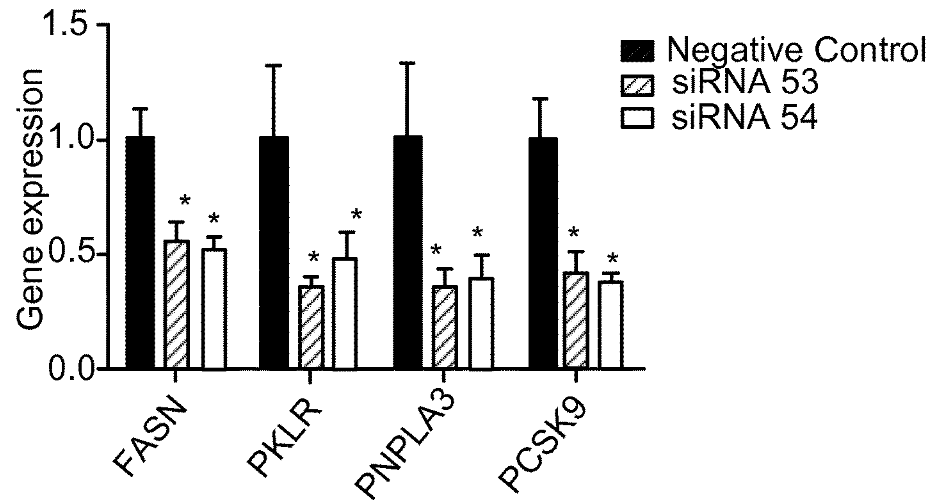
Figure 2H:
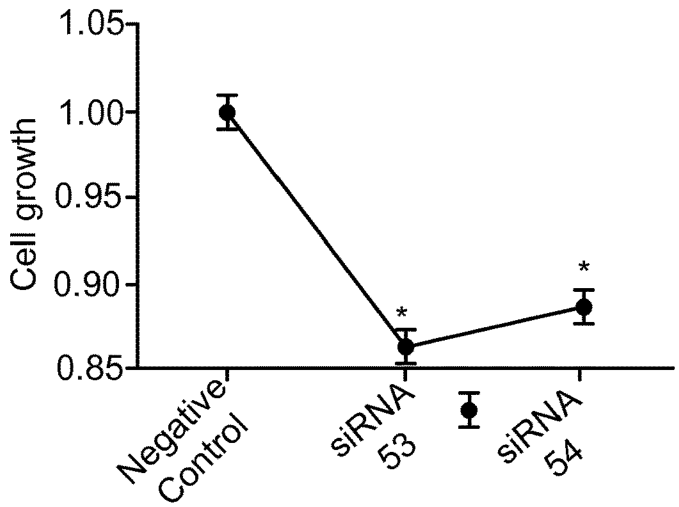

However, during the treatment of the cells with C75, other metabolic pathways may also have been regulated, and gene expression may have been affected by non-specific binding of C75. In this context, siRNA was used to decrease PKLR expression in the K562 cell line and it was observed that FASN expression (FIG. 2E) and cell growth (FIG. 2F) were significantly decreased, similarly to observations after treating the cells with C75. Moreover, PKLR expression was inhibited in the HepG2 cell line and it was found that FASN expression (FIG. 2G) and cell growth (FIG. 2H) were significantly decreased, as expected.

Validation of Physical Interactions in Mice and Human

Figure 3A:
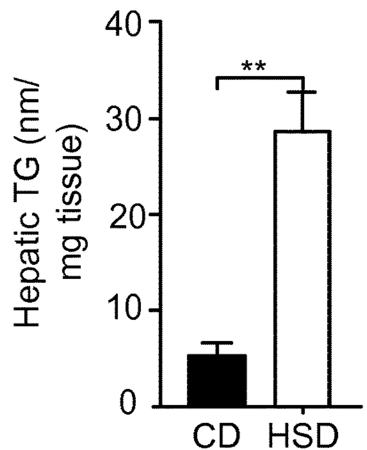
Figure 3B:
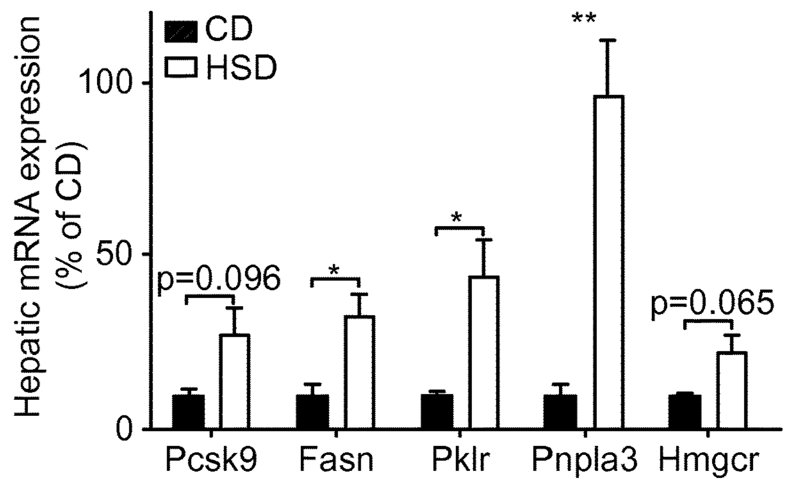

To show the functional relationship between FASN and the liver-specific targets identified here in vivo, mice (C57Bl/6N) were fed a zero-fat high sucrose diet (HSD) for two weeks that induced the development of fatty livers (FIG. 3A). Liver tissue samples were collected from the mice fed a HSD and the expression profiles of the genes in the liver of these mice were compared with those in the liver of mice fed a chow diet (CD). It was observed that liver TG content in the mice was significantly increased in the zero-fat diet group compared with the control (FIG. 3A). Next, the expression profiles of FASN and the liver-specific gene targets were determined and it was found that their expression levels were significantly increased in mice fed the HSD compared with mice fed the CD in parallel to the increase in liver fat (FIG. 3B).

Figure 3C:
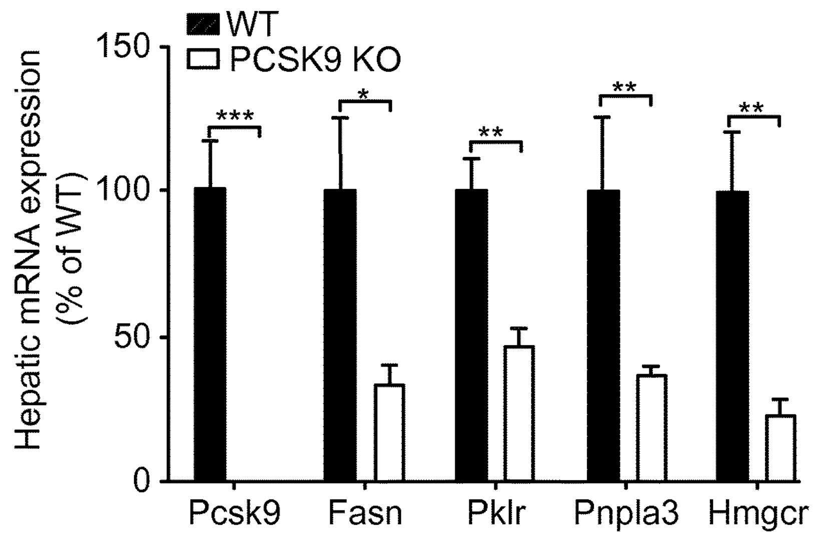
Figure 3D:
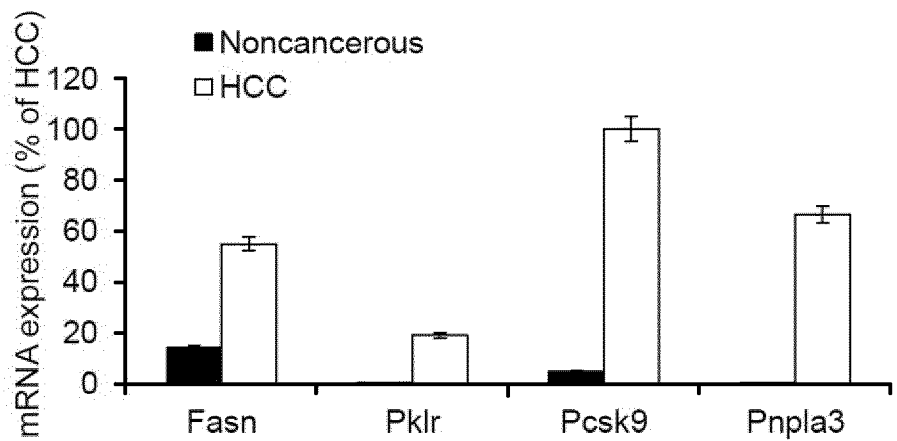

It has been reported that circulating PCSK9 levels increase with the severity of hepatic fat accumulation in patients at risk of NASH and PCSK9 mRNA levels in liver have been linked with steatosis severity (Ruscica et al, 2016). In this context, the wild type (WT) and PCSK9 knock-out (KO) mice were fed a CD for 10 weeks. Liver tissue samples were collected from the WT and PCSK9 KO mice and the expression levels of FASN and the other identified gene targets were analyzed. The expression levels of these genes in PCSK9 KO mice were determined and it was found that they were significantly downregulated (FIG. 3C). Hence, analysis suggested targeting of PCSK9 for the development of efficient treatment strategies for HCC patients.

Figure 3E:
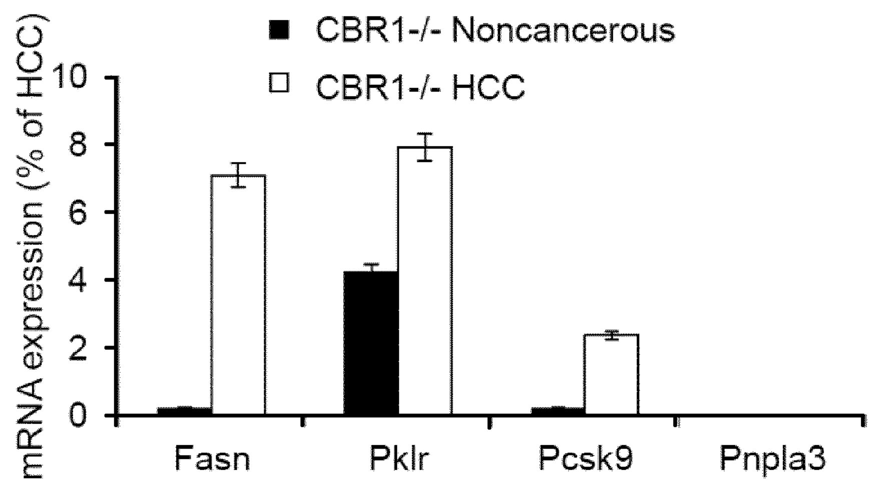

Endocannabinoids acting on hepatic the cannabinoid-1 receptor ($CB_1R$) promote DNL by increasing the expression of genes involved in lipid metabolism including FASN, SREBF1 and acetyl-CoA carboxylase-1 (ACACA) (Osei-Hyiaman et al, 2005). $CB_1R$ has been implicated in the pathology of different liver diseases with various etiologies including NAFLD (Osei-Hyiaman et al, 2008), AFLD (Jeong et al, 2008), viral hepatitis (Hezode et al, 2005), liver fibrosis (Teixeira-Clerc et al, 2006), cirrhosis (Giannone et al, 2012) and liver cancer (Mukhopadhyay et al, 2015). Activation of the endocannabinoid/$CB_1R$ system inhibits fatty acid I3-oxidation in the liver (Osei-Hyiaman et al, 2008), interrupts hepatic carbohydrate and cholesterol metabolism (Jourdan et al, 2012) and contributes to diet-induced obesity and NAFLD. It has been observed that activation of hepatic $CB_1R$ promoted the initiation and progression of chemically induced HCC in mice (Mukhopadhyay et al, 2015). Considering the associations between $CB_1R$, liver fibrosis and HCC even in the absence of obesity, the expression of Fasn as well as liver-specific gene targets in was analyzed animal models of liver cancer. The expression of the FASN and the liver-specific gene targets Pklr, Pcsk9 and Pnpla3 was measured, and it was found that their expression was significantly ($P<0.05$) increased in HCC tumor compared to adjacent noncancerous samples obtained from $CB_1R^{+/+}$ mice (FIG. 3D), with much smaller increases noted in corresponding samples $CB_1R^{-/-}$ mice. When the expression of these genes in was measured HCC tumor and noncancerous samples obtained from $CB_1R^{-/-}$ mice, it was found that the increase in the expression of FASN as well as liver-specific gene targets is attenuated in conjunction with the decrease in tumor growth $CB_1R^{-/-}$ mice (FIG. 3E).

Figure 3F:
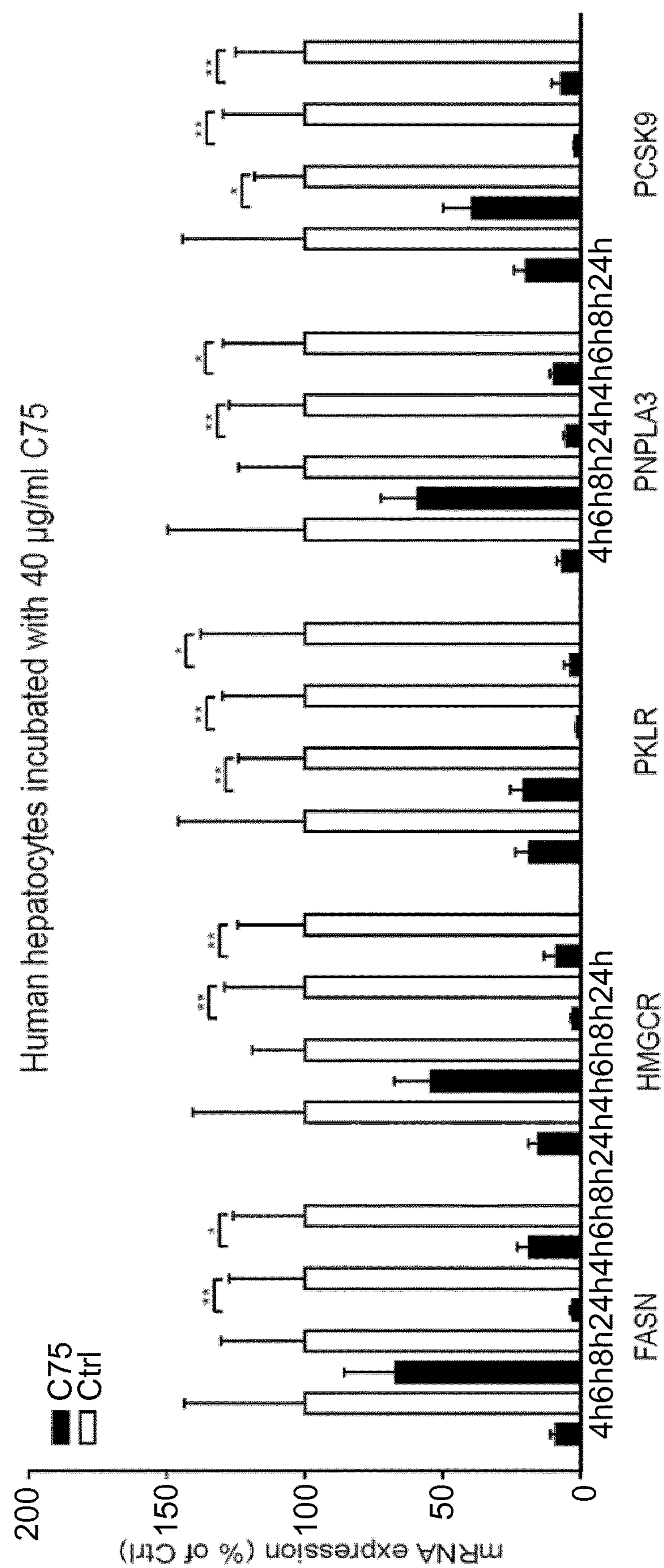

Finally, the predictions were validated by treating primary human hepatocytes with the FASN inhibitor C75 and it was found that the expression of FASN is interconnected with the expression of PKLR, PCSK9, PNPLA3 (FIG. 3F). Consequently, the expression of FASN can be decreased by silencing PKLR, PCSK9 or PNPLA3. Liver diseases connected to FASN can thus be treated (by silencing PKLR, PCSK9 or PNPLA3) without experiencing the side-effects associated with direct FASN inhibition.

Second Procedures

Cell Line Culture, Transfection and Proliferation Test

HepG2 cell line was purchased from ATCC and selected for subsequent genetic modification. Cells were routinely cultured in humidified incubator with 5% CO2 at 37°. Cells were maintained by RPMI 1640 medium (R2405, Sigma-Aldrich) with 10% fetal bovine serum (FBS, F7524, Sigma-Aldrich).

For downregulation of target genes, PKLR, PNPLA3, and PCSK9, RNAi experiment was performed by silencer pre-designed siRNA kit (Assay ID: 53 for PKLR, 121938 for PNPLA3 and 103966 for PCSK9, Thermo Fisher Scientific, USA). According to the manufacturer's instructions, HepG2 cells were treated by specific siRNA at 50 nM of final concentration using reverse transfection on the help of Lipofectamine RNAiMAX for 72 hours. Negative Control for transfection (4390843, Thermo Fisher Scientific, USA) was selected as standard for comparison from the same company.

Correspondingly, commercial expression plasmids with human tagged ORF clone were selected for upregulation of target genes (RG212337 for PKLR, RG209577 for PNPLA3, RC220000 for PCSK9; Origene, USA). According to instructions, cells were treated by plasmids respectively with concentration at 0.5 ug/ml on assistance of TurboFectin 8.0 (Origene, USA) and harvested for RNA isolation after 72 hours. Cloning Vector without any target sequence was served as internal negative control (PS100010, Origene, USA).

Subsequently, cell proliferation was measured by optical density (OD) value at 450 nm under a microplate reader (Chameleon, HIDEX) after incubation in medium with Cell Counting Kit-8 (CCK8) reagent (96992, Sigma) at 37° for 2 hours.

RNA Isolation and Quantitative Real-Time PCR (qPCR)

Cells were treated for experiment when they were grown to 80% confluence. RNA was isolated using RNeasy Plus Mini Kit (74136, Qiagen) according to manufacturer's protocol. Expressions of target genes were validated by quantitative real-time PCR (Schmittgen and Livak, 2008). To be specific, RNA was assayed using iTaq Universal SYBR green one-step kit (1725151, Bio-Rad) under commercialized Detection System (CFX Connect, Bio-Rad). And the relative expression of each gene was calculated by 2-ΔΔCT method described before (Schmittgen and Livak, 2008). β-actin was selected as internal reference gene for normalization.

Lipidomics Measurement on Cells with PKLR Down-regulation

To better clarify the genetic impact of PKLR on lipid deposition, cells were treated by siRNA and then tested by mass spectrometer for lipidomics data, sequentially. To be specific, HepG2 cells were transfected by siRNA (Assay ID: 53 with target on PKLR, applied by aforementioned method) for 72 hours and then harvested for lipidomics measurement. Correspondingly, cells treated with non-targeting siRNA (4390843, Thermo Fisher Scientific, USA) were assigned as control.

For lipidomics measurement, cells were extracted using butanol/methanol (BUME) as previously described (Lofgren et al., 2012). Internal standards (either deuterated or containing heptadecanoyl (C17:0) fatty acids) were added during the extraction. Analysis of triacylglycerols and phosphatidylcholines were made using direct infusion on a QTRAP 5500 mass spectrometer (Sciex, Concord, Canada) equipped with a robotic nanoflow ion source, the TriVersa NanoMate (Advion BioSciences, Ithaca, N.J.). Detection of triacylglycerols was made using neutral loss scanning in positive mode (Murphy et al., 2007). Phosphatidylcholines were analyzed in positive mode using m/z 184 (phosphocholine) as fragment ion (Brugger et al., 1997).

Statistical Analysis of qPCR Assay and Cell Proliferation Test

All results of measurement were presented/shown by mean±SD and One-way ANOVA was applied for comparisons in quantitative covariates. All experiments were repeated independently for three times and samples were assigned by triplicates for each group. Calculation was performed by SPSS 17.0 (IBM Corporation, USA) and $P<0.05$ was considered as significance on comparison across different groups.

Transcript Profiling (RNA-Seq) of hepG2 Cells with Target Gene Perturbations

Total 24 samples of HepG2 cell line with the inhibition and over-expression of target genes, PKLR, PNPLA3, and PCSK9, with three replicates per each perturbation were sequenced using Illumina HiSeq 2500 High Output Mode, at paired-end 2×125bp. To be specific, strand-specific RNA libraries were prepared by poly-A selection from isolated RNAs and sample quality was assayed by RNA 6000 nano kit on 2100 bioanalyzer instruments (Agilent Technologies, USA). And samples with RNA integrity number (RIN)>8 were considered to be qualified for sequencing. Subsequently, paired-end raw sequencing data (FASTQ files) was processed and quantified into transcripts per million (TPM) values and raw read count values by Kallisto software, using human reference (GRCh38) from GENCODE version 24 (Harrow et al., 2012).

Generation of HepG2 Transcriptional Regulatory Network from DNase-Seq

A transcriptional regulatory network (TRN) data for HepG2 cell line was generated based on the DNase-seq from ENCODE consortium (Consortium, 2012; Neph et al., 2012b) and human transcription factor motifs from HOCOMOCO (Kulakovskiy et al., 2018) and motifDB (R MotifDb package). First, the whole genome sequences were scanned with human transcription factor motifs by Find Individual Motif Occurrences (FIMO) program from MEME Suite (Grant et al., 2011), in order to extract individual matches to each motif. The positions of matched motifs with statistical significance of 0.05 (adjusted P-Value, FDR) were selected as significant matches. Secondly, genomic footprints from DNase-seq of HepG2 cell line were identified based on footprint occupancy scores calculated by using the Wellington footprinting approach (Piper et al., 2013). Subsequently, both selected transcription factor motifs and genomic footprints were combined to profile potential binding sites of the transcription factors. Lastly, the binding sites of transcription factor motif were annotated with nearby protein-coding genes (maximum distance +/−5 kbps from Transcriptional Start Site (TSS)) of Ensembl (Zerbino et al., 2015), as potential target genes, and annotated pairs of given transcription factors and target genes were used to construct HepG2 TRN.

Co-Regulation Analysis

Among target genes of HepG2 TRN, the number of shared TFs of given target gene pairs was counted, which was called co-regulation strength (Lee et al., 2016). Based on co-regulation strengths, scores of each KEGG pathway were checked and compared with background co-regulation strengths by KS test (Lee et al., 2016) and chose those with most significantly high co-regulation strengths ($P<0.01$)

Reporter Transcription Gactor (TF) Analysis

Based on generated HepG2 TRN data, reporter transcription factor (TF) analysis (Huang et al., 2017) was performed, which identified significant expression changes of target genes per each TF. Any TFs or target genes having their gene expressions in TPM unit less than one, regarding as not-detected genes, were filtered out. Reporter TF analysis was performed using PIANO R package (Varemo et al., 2013) and identified significant TFs ($P<0.05$) in either directional or non-directional changes. Finally, the reporter TFs significant in both inhibition and over-expression of PKLR were chosen.

Reconstruction of GEM for HepG2 Cell Line

Cell line specific GEM for HepG2 was reconstructed based on the RNA-seq data generated in this study and a previously developed task-driven model reconstruction (tINIT) algorithm (Agren et al., 2014). The tINIT algorithm employs defined metabolic tasks for imposing constraints on the functionality of the reconstructed models. In this specific case, the input of the growth task was changed from Ham's media to RPMI 1640. In order to generate a consensus GEM for HepG2 that could be a good representative in this study, RNA-Seq data from for all investigated conditions was merged by selecting the maximum expression of each gene among all conditions. The adapted metabolic tasks, the merged RNA-Seq data and a generic GEM for human cancer were used as input for the tINIT algorithm, and as a result, a HepG2 specific GEM had been generated.

Metabolic Flux Analysis Using GEM of HepG2

The uptake constraints for GEM of HepG2 was calculated and adapted based on the medium component. Transcriptomic changes before and after PKLR siRNA inhibition were integrated into the model using a previously established method, RMetD (Mardinoglu et al., 2015). In short, RMetD considers the significantly changed genes as constraint changes in GEMs and generates two condition specific models. Then the flux distributions for both models were sampled 10,000 times (Bordel et al., 2010) and the flux in each corresponding condition was calculated as the mean of the sampled fluxes.

Second Results

Perturbation of PKLR, PNPLA3 and PCSK9 in HepG2 Cells

In order to study the effect of potential perturbation of the liver-specific genes including PKLR, PNPLA3, and PCSK9, the expression of each gene in HepG2 cells was inhibited and over-expressed. si-RNAs for these liver-specific genes were synthesized and respective gene expressions in HepG2 cells were silenced. The effects of si-RNA transfections were evaluated by quantitative real-time PCR assay a significant down-regulation was observed, compared to cells treated by negative control (96%, 93%, and 94% inhibitory rates, respectively; all P<0.05). For over-expression of the target genes, HepG2 cells were transfected by expression plasmids with PKLR, PNPLA3, and PCSK9 and the expression of the target genes showed a significant up-regulations compared to cells treated by empty cloning vector (1694.3, 859.8, and 4.8 folds, respectively; all P<0.05).

Cell viability after transfections of siRNA and expression plasmid for 72 hours were tested and significant changes were observed. In groups with downregulation of the target genes, siRNA significantly inhibited the HepG2 cell viability compared to cells treated by negative control (inhibitory rate ranged from 14%-23%. While in group with upregulation of target genes, expression plasmids with targeted ORFs had significant promotion on HepG2 cell growth (ranged from 43%-73%) compared to cells interfered only by empty vector with the available sequence.

The total lipid content was also measured with inhibition of PKLR, a key driver enzyme involved in the development of NAFLD. The cells were treated with effective siRNA (ID: 53 with target on PKLR) and non-targeting negative control, measured the total triglycerides and found that downregulation of PKLR caused significant decrease in the triglyceride level (P<0.05).

Compared to a group with negative control, the total triglyceride was decreased about 15% in cells with PKLR downregulation after adjusting based on the phosphatidylcholines levels (471.7±45.5 vs. 555.0±51.2).

Revealing the Altered Biological Functions in Response to Modulation of Genes

To study the altered biological changes in response to the perturbation of the three liver-specific genes, RNA-Seq data was generated before and after the inhibition and over expression using triplicates. RNA-Seq data was processed using Kallisto software (Bray et al., 2016) and gene expressions were quantified by transcripts per million (TPM) values. During the quality control of the data, principal component analysis on log-transformed TPM values was performed and the corresponding batch effect showing distinct expression pattern was removed. Based on TPM values, the expression of target genes and FASN was checked. It was confirmed that expression of FASN was significantly changed by the perturbation of the PKLR and PCSK9, whereas it was not significantly changed with the perturbation of the PNPLA3. Moreover, expression of PKM, catalyzing the same reaction as PKLR in HepG2 cells, was checked and it was found its expression is not significantly affected by the knockdown of target genes.

To reveal the changes in global gene expression profiling, significantly (Adjusted $P<1\times10^{-8}$) differentially expressed genes (DEGs) were identified in each condition using R DESeq package (Anders and Huber, 2010). In total 3,359 genes and 4,264 genes were differentially expressed with inhibition and over-expression of PKLR; 4,217 genes and 2,139 genes by inhibition and over-expression of PNPLA3; whereas 760 genes and 2,802 genes by inhibition and over-expression of PCSK9, respectively. Interestingly, majority of the DEGs with inhibition and over-expression of target genes were significantly (hypergeometric test $P<1\times10^{-20}$) overlapped (2,437, 1,745 and 627 genes for PKLR, PNPLA3, and PCSK9, respectively. Notably, all fold changes with inhibition and over-expression of a target gene were significantly correlated (Spearman's correlation coefficients (r): −0.73, −0.70, and −0.69 for PKLR, PNPLA3, and PCKS9, respectively), indicating a coordinated global expression changes by perturbation of a single target gene.

To investigate shared biological processes associated with DEGs across all different perturbations, gene ontology enrichment test was performed using DAVID (Huang da et al., 2009a, b). Among shared enriched GO terms, it was observed that cholesterol metabolism, DNA replication and fatty acid metabolism were significantly (FDR<0.01) enriched with upregulated genes, whereas regulation of apoptosis and positive regulation of transcription were significantly (FDR<0.01) enriched with downregulated genes, implying apoptosis and negative feedback regulation. Biological process enriched specifically with the perturbation of each target gene was also observed. For example, telomerase maintenance and liver regeneration were associated with DEGs in the over-expression of PKLR and PNPLA3, respectively whereas epithelial cell differential was associated with DEGs only in the over-expression of PCSK9.

It was also checked if DEGs of any conditions are significantly overlapped with tissue-specific genes (i.e. in tissue enriched/enhanced and group-enriched categories) introduced in the Human Protein Atlas (Uhlen et al., 2015)). It was found that DEGs of all cases were significantly (Hypergeometric tests, P<0.05) enriched with tissue-specific genes in eight different tissues including liver, kidney, duodenum, small intestine, placenta, gall bladder, pancreas, and bone marrow. As expected, liver tissue was the most significant (Hypergeometric test, $P<1\times10^{-20}$) among them, showing that perturbation of our targets in HepG2 is representing changes in liver-specific genes. In addition, it was checked if DEGs of each condition is enriched in any subcellular locations based on spatial human proteome map from the Cell Atlas (Thul et al., 2017) and found that DEGs in different conditions were significantly (Hypergeometric tests, P<0.05) enriched with mitochondria, plasma membrane, cytoskeleton and cytoplasm. Of note, DEGs identified from both inhibition and over-expression of PKLR were significantly enriched in mitochondria (P<0.05), indicating coordinated regulations of mitochondrial genes with the perturbation of PKLR.

It was observed that DEGs and associated biological processes were largely shared between different perturbations of target genes including PKLR, PNPLA3 and PCSK9. Shared DEGs and the associated biological processes among all target genes were checked. It was observed that total 498 DEGs were shared among all target genes and found that 404 of those genes were significantly positively correlated with the perturbation of the target gene, whereas remaining 94 of the genes were negatively correlated. It was found that those 404 genes were significantly (FDR<0.05) enriched in DNA replication, cholesterol metabolism, fatty acid metabolism, and cell cycle, whereas 94 genes were significantly enriched in various regulations of macromolecules and signal transduction based on DAVID gene ontology enrichment test (Huang da et al., 2009a, b). It was thus observed that perturbation of PKLR, PNPLA3, and PCSK9 might induce changes in lipid metabolism and cell cycle and other key pathogenic pathways involved in the development of NAFLD and HCC.

The Mechanistic Changes by PKLR Modulation were Shared with FASN Co-Expression network in HCC Based on the analysis, it was found that potential perturbation of PKLR, PNPLA3, and PCSK9 affect key pathways involved in liver diseases and may provide beneficial effect in the treatment of such diseases. However, the expression of FASN was not significantly changed by the perturbation of PNPLA3 (adjusted P-values for over-expressing and inhibiting PNPLA3: 0.38 and 0.054, respectively) and highly affected by the perturbation of PKLR. The overlap between DEGs for each target gene with top-100 FASN co-expressed genes in HCC tumors from our previous study (Lee et al., 2017) was checked and it was found that DEGs of PKLR perturbation have the most overlap with the co-expressed genes with FASN (45 genes). Notably, DEGs positively correlated with PKLR perturbation were mostly overlapped with FASN co-expressed genes (43 genes), whereas DEGs negatively correlated with PKLR perturbation were rarely overlapped (2 genes). The overlapped biological process associated with the DEGs genes and FASN co-expressed genes was also checked using DAVID analysis (FDR<0.05) and it was found that DEGs of PKLR perturbation has more overlap with the FASN co-expressed genes in terms of enriched biological processes, up to 89% (17 processes), which were mostly associated with lipid/cholesterol metabolism. Three biological processes only overlapped between DEGs of PKLR perturbation and FASN co-expressed genes were Acyl-CoA biosynthesis, thioester biosynthesis and Acetyl-CoA metabolism, which are fundamental parts of lipid synthesis. Next, unique GO terms enriched in DEGs of PKLR, PNPLA3 and PCSK9 were checked. More unique terms were found for PKLR (total 39 and 16 GO terms for PKLR and PNPLA3, respectively), but many of them were related to lipid metabolism and cell growth, including DNA metabolism, apoptosis, signaling and immune response. For PNPLA3, unique GO terms including liver development, carbohydrate metabolism, skeletal muscle cell differentiation, and response to lipopolysaccharide, showing much diverse spectrum. For PCSK9, none of terms were unique in DEGs of its perturbation.

Generation of Integrated Network (IN) for HepG2 Cell Line

Tissue-specific INs have been valuable resources to investigate underlying mechanism of diseases, including obesity, insulin resistance, and type-2 diabetes (Lee et al., 2016b). Here an IN of HepG2 cells as a model for HCC was generated and possible mechanistic changes in HCC was investigated by inhibiting a specific target gene, in this case PKLR. DNase-seq data of HepG2 cells was retrieved from ENCODE database (ID: ENCSR000ENP) and the genomic footprints of HepG2 cells were profiled by a digital genomic footprinting (DGF) algorithm, Wellington algorithm (Piper et al., 2013) to identify binding regions of each TFs. Human transcription factor (TF) motifs from HOCOMOCO and MotifDB (Jolma et al., 2013; Kulakovskiy et al., 2018; Neph et al., 2012a; Portales-Casamar et al., 2010; Robasky and Bulyk, 2011; Xie et al., 2010) were scanned over the whole human genome (adjusted P<0.05) and the genomic footprints identified based on DNase-seq data were annotated. From annotated genomic footprints, TRN of HepG2 cells, which includes 747 TFs and 8,409 target genes, total 8,988 genes, was constructed.

A HepG2 specific GEM based on here generated RNA-seq data and generic human model HMR2 (Mardinoglu et al., 2014) was also generated to study the global of metabolic alterations. GEM for HepG2 referred as iHepG2 included 1,614 unique metabolites, 4,095 metabolic reactions and 1,917 metabolic genes associated with those reactions. The overlap between the genes in TRN and GEM for HepG2 was checked and 661 genes shared between the two networks were found.

PPIN for HepG2 cells was finally generated using the generic PPIN for human (Rolland et al., 2014), filtering out proteins less than average 1 TPM in knock-down and over-expression controls. The resulting PPIN included 2,964 proteins and their links between other proteins, (7,137 interactions). It was also found that 371 genes were shared between the PPIN and metabolic model of HepG2 cells. Through the merging of GEM, TRN and PPIN for HepG2 cells, IN for HepG2 cells was generated and the key genes affected by the inhibition and overexpression of PKLR in HepG2 cells were investigated.

Potential Effect of the PKLR Inhibition Using INs

Based on co-regulations of TFs and proteins in INs, highly regulated and tissue-specific pathways in liver, muscle and adipose tissue were identified in insulin resistant subjects (Lee et al., 2016b). Here pathways (e.g. KEGG) with highly co-regulations in HepG2 cells (Kolmogorov-Smirnov (KS) tests, adjusted P<0.01) were identified based on here generated HepG2 specific IN, and the most significant pathways including metabolic pathways, RAS signaling pathways and cell cycle were identified, showing the characteristics of a cancer cell line.

Using IN for HepG2, coordinated expression changes of TFs (Huang et al., 2017) in specific condition, such as inhibition of PKLR, were investigated. Using DEGs with the inhibition of PKLR and reporter TFs algorithm (Huang et al., 2017; Varemo et al., 2013), 112 TFs where their target gene expressions were significantly (P<0.05) changed were identified. Based on DAVID gene ontology enrichment tests, target genes bound more than three reporter TFs (807 genes) were enriched in nucleic acid metabolism and cell cycle. It was found that SP1, TFDP1, NRF1, PPARA, PPARD, EGR1 and FOXO4 showed correlated expression changes of its target genes and these TFs were known as regulators of lipid homeostasis, redox balance and proliferation (e.g. TGF-beta pathway) (Carlsson and Mahlapuu, 2002; Desvergne and Wahli, 1999; Lu and Archer, 2010; Scarpulla, 2002; Thiel and Cibelli, 2002; Wu et al., 1995).

In order to investigate the global metabolic response to PKLR inhibition, the transcriptomic data were integrated into HepG2 IN and the flux changes were calculated using RMetD (Mardinoglu et al., 2015). The flux from pyruvate to PEP is decreased after PKLR inhibition. As a result, the fluxes through tricarboxylic acid (TCA) cycle and oxidative phosphorylation are significantly down-regulated, since the inhibition of PKLR expression decreased the inflow of pyruvate into mitochondria. The flux goes to oxidative phosphorylation which is partly regulated by the reporter TF, NRF1 is also down-regulated, correspondingly. The predicted in silico cell growth is also decreased with PKLR inhibition, which is consistent with experimental observation and in good agreement with the results of GO term enrichment analysis. This is potentially linked to the change of regulatory effect of reporter TFs including SP1, TFDP1, EGR1 and FOXO4. In addition, it was observed that the flux through fatty acids biosynthesis is down regulated due to lack of precursor. Surprisingly, the flux through fatty acid beta oxidation is also decreased. The decreased flux together with the positively correlated reporter TFs, PPARA and PPARD, implicated a potential novel regulatory mechanism of fatty acid beta oxidation that is related to PKLR expression. Moreover, the flux through pentose phosphate pathway and second half of glycolysis is increased disregarding the down-regulation of several key enzymes. After tracing the predicted fluxes, it was found that there is a metabolic flux shift from the second half of glycolysis to the first half of PP pathway, to enable more NADPH production. This increased NADPH production is compensating the decrease of in folate cycle which is an important source of NADPH.

Furthermore, it was found that there is another metabolic flux shift from nucleotide synthesis to the second half of PP pathway. This is rational for the cell, since it is economic to redirect the flux from DNA synthesis caused by decreased cell growth to glycolysis for other purposes. The enhanced glycolysis pathway together with the decreased flux from PEP to pyruvate leads to an increased flux to PEP, and this is balanced with the largely decreased PEP flux coming from fatty acids synthesis. It has been suggested that the decreased flux in glycolysis may be compensated by increased fatty oxidation and uptake of branch amino acids and serine. That is however not the case with PKLR inhibition according to the flux analysis result in HepG2 cells. Of note, most of the mitochondria metabolic fluxes are decreased, which is consistent with the subcellular localization enrichment analysis result. It was also found that the hypoxia regulator, HIF1A and its target, PDK are both up-regulated. HIF1A is known to be a key regulator for mitochondria metabolism (Semenza, 2011), and it is also regulated by the reporter TF, FOXO4.

REFERENCES

Agren R, Bordel S, Mardinoglu A, Pornputtapong N, Nookaew I, Nielsen J (2012) Reconstruction of Genome-Scale Active Metabolic Networks for 69 Human Cell Types and 16 Cancer Types Using INIT. Nos Comput Biol 8: e1002518

Agren R, Mardinoglu A, Asplund A, Kampf C, Uhlen M, Nielsen J (2014) Identification of anticancer drugs for hepatocellular carcinoma through personalized genome-scale metabolic modeling. Mol Syst Biol 10: 721

Akinc, A. et al. (2008) A combinatorial library of lipid-like materials for delivery of RNAi therapeutics. Nat. Biotechnol. 26, 561-569

Anders S, Huber W (2010) Differential expression analysis for sequence count data. Genome Biol 11: R106

Aragones G, Auguet T, Armengol S, Berlanga A, Guiu-Jurado E, Aguilar C, Martinez S, Sabench F, Porras J A, Ruiz M D, Hernandez M, Sirvent J J, Del Castillo D, Richart C (2016) PNPLA3 Expression Is Related to Liver Steatosis in Morbidly Obese Women with Non-Alcoholic Fatty Liver Disease. Int J Mol Sci 17

Batra et al. (2017) Elimination of Toxic Microsatellite Repeat Expansion RNA by RNA-Targeting Cas9, Cell Björnson E, Mukhopadhyay B, Asplund A, Pristovsek N, Cinar R, Romeo S, Uhlen M, Kunos G, Nielsen J, Mardinoglu A (2015) Stratification of hepatocellular carcinoma patients based on acetate utilization. Cell Rep 13: 2014-2026

Bordbar A, Monk J M, King Z A, Palsson B O (2014) Constraint-based models predict metabolic and associated cellular functions. Nat Rev Genet 15: 107-120

Bordel, S., Agren, R., and Nielsen, J. (2010). Sampling the solution space in genome-scale metabolic networks reveals transcriptional regulation in key enzymes. PLoS Comput Biol 6, e1000859

Brugger, B., Erben, G., Sandhoff, R., Wieland, F. T., and Lehmann, W. D. (1997). Quantitative analysis of biological membrane lipids at the low picomole level by nano-electrospray ionization tandem mass spectrometry. Proc Natl Acad Sci USA 94, 2339-2344

Carlsson, P., and Mahlapuu, M. (2002). Forkhead transcription factors: key players in development and metabolism. Dev Biol 250, 1-23

Consortium, E. P. (2012). An integrated encyclopedia of DNA elements in the human genome. Nature 489, 57-74

Desvergne, B., and Wahli, W. (1999). Peroxisome proliferator-activated receptors: nuclear control of metabolism. Endocr Rev 20, 649-688

Dorn C, Riener M O, Kirovski G, Saugspier M, Steib K, Weiss T S, Gabele E, Kristiansen G, Hartmann A, Hellerbrand C (2010) Expression of fatty acid synthase in nonalcoholic fatty liver disease. Int J Clin Exp Pathol 3: 505-514

Elsemman I E, Mardinoglu A, Shoaie S, Soliman T H, Nielsen J (2016) Systems biology analysis of hepatitis C virus infection reveals the role of copy number increases in regions of chromosome 1q in hepatocellular carcinoma metabolism. Mol Biosyst 12: 1496-1506

Dowdy (2017) Overcoming cellular barriers for RNA therapeutics. VOLUME 35, NUMBER 3, MARCH 2017, nature biotechnology Giannone F A, Baldassarre M, Domenicali M, Zaccherini G, Trevisani F, Bernardi M, Caraceni P (2012) Reversal of liver fibrosis by the antagonism of endocannabinoid CB1. receptor in a rat model of CCl (4)-induced advanced cirrhosis. Lab Invest 92: 384-395

Grant, C. E., Bailey, T. L., and Noble, W. S. (2011). FIMO: scanning for occurrences of a given motif. Bioinformatics 27, 1017-1018

GTEx (2013) The Genotype-Tissue Expression (GTEx) project. Nat Genet 45: 580-585

Harriman G, Greenwood J, Bhat S, Huang X, Wang R, Paul D, Tong L, Saha A K, Westlin W F, Kapeller R, Harwood H J, Jr. (2016) Acetyl-CoA carboxylase inhibition by ND-630 reduces hepatic steatosis, improves insulin sensitivity, and modulates dyslipidemia in rats. P Natl Acad Sci USA 113: E1796-1805

Hezode C, Roudot-Thoraval F, Nguyen S, Grenard P, Julien B, Zafrani E S, Pawlotsky J M, Dhumeaux D, Lotersztajn S, Mallat A (2005) Daily cannabis smoking as a risk factor for progression of fibrosis in chronic hepatitis C. Hepatology 42: 63-71

Huang D W, Sherman B T, Lempicki R A (2009) Systematic and integrative analysis of large gene lists using DAVID bioinformatics resources. Nat Protoc 4: 44-57

Huang, M., Bao, J., Hallstrom, B. M., Petranovic, D., and Nielsen, J. (2017). Efficient protein production by yeast requires global tuning of metabolism. Nat Commun 8, 1131

Huang da, W., Sherman, B. T., and Lempicki, R. A. (2009a). Bioinformatics enrichment tools: paths toward the comprehensive functional analysis of large gene lists. Nucleic Acids Res 37, 1-13.

Huang da, W., Sherman, B. T., and Lempicki, R. A. (2009b). Systematic and integrative analysis of large gene lists using DAVID bioinformatics resources. Nat Protoc 4, 44-57.

Hyötyläinen T, Jerby L, Petäjä E M, I. M, Jantti S, Auvinen P, Gastaldelli A, Yki-Järvinen H, Ruppin E, Orešič M (2016) Genome-scale study reveals reduced metabolic adaptability in patients with non-alcoholic fatty liver disease. Nat Commun 7: 8994

Jeong W I, Osei-Hyiaman D, Park O, Liu J, Batkai S, Mukhopadhyay P, Horiguchi N, Harvey-White J, Marsicano G, Lutz B, Gao B, Kunos G (2008) Paracrine activation of hepatic CB1. receptors by stellate cell-derived endocannabinoids mediates alcoholic fatty liver. Cell Metab 7: 227-235

Jourdan T, Demizieux L, Gresti J, Djaouti L, Gaba L, Verges B, Degrace P (2012) Antagonism of peripheral hepatic cannabinoid receptor-1 improves liver lipid metabolism in mice: evidence from cultured explants. Hepatology 55: 790-799

Juliano, R. L. (2016) The delivery of therapeutic oligonucleotides. Nucleic Acids Res. 44, 6518-6548

Kampf C, Mardinoglu A, Fagerberg L, Hallstrom B, Edlund K, Nielsen J, Uhlen M (2014) The human liver-specific proteome defined by transcriptomics and antibody-based profiling. Faseb J 28: 2901-2914

Kew M C (2010) Epidemiology of chronic hepatitis B virus infection, hepatocellular carcinoma, and hepatitis B virus-induced hepatocellular carcinoma. Pathol Biol (Paris) 58: 273-277

Khlaiphuengsin A, Kiatbumrung R, Payungporn S, Pinjaroen N, Tangkijvanich P (2015) Association of PNPLA3 Polymorphism with Hepatocellular Carcinoma Development and Prognosis in Viral and Non-Viral Chronic Liver Diseases. Asian Pac J Cancer Prev 16: 8377-8382

Khvorova A, J K Watts (2017) The chemical evolution of oligonucleotide therapies of clinical utility, VOLUME 35, NUMBER 3, MARCH, nature biotechnology Kulakovskiy, I. V., Vorontsov, I. E., Yevshin, I. S., Sharipov, R. N., Fedorova, A. D., Rumynskiy, E. I., Medvedeva, Y. A., Magana-Mora, A., Bajic, V. B., Papatsenko, D. A., et al. (2018). HOCOMOCO: towards a complete collection of transcription factor binding models for human and mouse via large-scale ChIP-Seq analysis. Nucleic Acids Res 46, D252-D259

Lee S, Zhang C, Kilicarslan M, Bluher M, Uhlen M, Nielsen J, Smith U, Serlie M J, Boren J, Mardinoglu A (2016) Integrated network analysis reveals an association between plasma mannose levels and insulin resistance. Cell Metab 24: 172-184

Lee, S., Zhang, C., Kilicarslan, M., Piening, B. D., Björnson, E., Hallstrom, B. M., Groen, A. K., Ferrannini, E., Laakso, M., Snyder, M., et al. (2016b). Integrated Network Analysis Reveals an Association between Plasma Mannose Levels and Insulin Resistance. Cell Metab 24, 172-184.

Lofgren, L., Stahlman, M., Forsberg, G. B., Saarinen, S., Nilsson, R., and Hansson, G. I. (2012). The BUME method: a novel automated chloroform-free 96-well total lipid extraction method for blood plasma. J Lipid Res 53, 1690-1700

Lu, S., and Archer, M. C. (2010). Sp1 coordinately regulates de novo lipogenesis and proliferation in cancer cells. Int J Cancer 126, 416-425

Semple, S. C. et al. (2010) Rational design of cationic lipids for siRNA delivery. Nat. Biotechnol. 28, 172-176

Mardinoglu A, Agren R, Kampf C, Asplund A, Nookaew I, Jacobson P, Walley A J, Froguel P, Carlsson L M, Uhlen M, Nielsen J (2013a) Integration of clinical data with a genome-scale metabolic model of the human adipocyte. Mol Syst Biol 9: 649

Mardinoglu A, Agren R, Kampf C, Asplund A, Uhlen M, Nielsen J (2014a) Genome-scale metabolic modelling of hepatocytes reveals serine deficiency in patients with non-alcoholic fatty liver disease. Nat Commun 5: 3083

Mardinoglu A, Björnson E, Zhang C, Klevstig M, Soderlund S, Stahlman M, Adiels M, Hakkarainen A, Lundbom N, Kilicarslan M, Hallstrom B M, Lundbom J, Verges B, Barrett P H, Watts G F, Serlie M J, Nielsen J, Uhlen M, Smith U, Marschall H U et al (2017a) Personal model-assisted identification of NAD+ and glutathione metabolism as intervention target in NAFLD. Mol Syst Biol 13: 916

Mardinoglu A, Boren J, Smith U, Uhlen M, Nielsen J (2017b) The employment of systems biology in gastroenterology and hepatology. Nat Rev Gastroenterol Hepatol In press Mardinoglu A, Gatto F, Nielsen J (2013b) Genome-scale modeling of human metabolism—a systems biology approach. Biotechnol J 8: 985-996

Mardinoglu A, Kampf C, Asplund A, Fagerberg L, Hallstrom B M, Edlund K, Bluher M, Ponten F, Uhlen M, Nielsen J (2014b) Defining the human adipose tissue proteome to reveal metabolic alterations in obesity. J Proteome Res 13: 5106-5119

Mardinoglu A, Nielsen J (2012) Systems medicine and metabolic modelling. J Intern Med 271: 142-154

Mardinoglu A, Nielsen J (2015) New paradigms for metabolic modeling of human cells. Curr Opin Biotech 34: 91-97

Mardinoglu A, Nielsen J (2016) Editorial: The Impact of Systems Medicine on Human Health and Disease. Front Physiol 7: 552

Mardinoglu A, Shoaie S, Bergentall M, Ghaffari P, Zhang C, Larsson E, Backhed F, Nielsen J (2015) The gut microbiota modulates host amino acid and glutathione metabolism in mice. Mol Syst Biol 11: 834

Matsuda, S. et al. (2015) iRNA conjugates carrying sequentially assembled trivalent N-acetylgalactosamine linked through nucleosides elicit robust gene silencing in vivo in hepatocytes. ACS Chem. Biol. 10, 1181-1187

Mukhopadhyay B, Schuebel K, Mukhopadhyay P, Cinar R, Godlewski G, Xiong K, Mackie K, Lizak M, Yuan Q, Goldman D, Kunos G (2015) Cannabinoid receptor 1 promotes hepatocellular carcinoma initiation and progression through multiple mechanisms. Hepatology 61: 1615-1626

Murphy, R. C., James, P. F., McAnoy, A. M., Krank, J., Duchoslav, E., and Barkley, R. M. (2007). Detection of the abundance of diacylglycerol and triacylglycerol molecular species in cells using neutral loss mass spectrometry. Anal Biochem 366, 59-70.

Mäkilä, J. et al. (2014) Synthesis of multi-galactose-conjugated 2'-O-methyl oligoribonucleotides and their in vivo imaging with positron emission tomography. Bioorg. Med. Chem. 22, 6806-6813

Nair, J. K. et al. (2014) Multivalent N-acetylgalactosamine-conjugated siRNA localizes in hepatocytes and elicits robust RNAi-mediated gene silencing. J. Am. Chem. Soc. 136, 16958-16961

Neph, S., Vierstra, J., Stergachis, A. B., Reynolds, A. P., Haugen, E., Vernot, B., Thurman, R. E., John, S., Sandstrom, R., Johnson, A. K., et al. (2012b). An expansive human regulatory lexicon encoded in transcription factor footprints. Nature 489, 83-90.

Nielsen J (2017) Systems Biology of Metabolism: A Driver for Developing Personalized and Precision Medicine. Cell Metab 25: 572-579

O'Brien E J, Monk J M, Palsson B O (2015) Using Genome-scale Models to Predict Biological Capabilities. Cell 161: 971-987

Osei-Hyiaman D, DePetrillo M, Pacher P, Liu J, Radaeva S, Batkai S, Harvey-White J, Mackie K, Offertaler L, Wang L, Kunos G (2005) Endocannabinoid activation at hepatic CB1. receptors stimulates fatty acid synthesis and contributes to diet-induced obesity. The Journal of clinical investigation 115: 1298-1305

Osei-Hyiaman D, Liu J, Zhou L, Godlewski G, Harvey-White J, Jeong W I, Batkai S, Marsicano G, Lutz B, Buettner C, Kunos G (2008) Hepatic CB1. receptor is required for development of diet-induced steatosis, dyslipidemia, and insulin and leptin resistance in mice. The Journal of clinical investigation 118: 3160-3169

Pandey P R, Liu W, Xing F, Fukuda K, Watabe K (2012) Anti-cancer drugs targeting fatty acid synthase (FAS). Recent Pat Anticancer Drug Discov 7: 185-197

Petrick J L, Kelly S P, Altekruse S F, McGlynn K A, Rosenberg P S (2016) Future of Hepatocellular Carcinoma Incidence in the United States Forecast Through 2030. Journal of Clinical Oncology 34: 1787-+

Piper, J., Eke, M. C., Cauchy, P., Cockerill, P. N., Bonifer, C., and Ott, S. (2013). Wellington: a novel method for the accurate identification of digital genomic footprints from DNase-seq data. Nucleic Acids Res 41, e201.

Pons P, Latapy M (2005) Computing communities in large networks using random walks. Computer and Information Sciences-Iscis 2005, Proceedings 3733: 284-293

Prakash, T. P. et al. (2014) Targeted delivery of antisense oligonucleotides to hepatocytes using triantennary N-acetyl galactosamine improves potency 10-fold in mice. Nucleic Acids Res. 42, 8796-8807

Prakash, T. P. et al. (2016) Synergistic effect of phosphorothioate, 5'-vinylphosphonate and GalNAc modifications for enhancing activity of synthetic siRNA. Bioorg. Med. Chem. Lett. 26, 2817-2820

Rajeev, K. G. et al. (2015) Hepatocyte-specific delivery of siRNAs conjugated to novel non-nucleosidic trivalent N-acetylgalactosamine elicits robust gene silencing in vivo. ChemBioChem 16, 903-908

Ruscica M, Ferri N, Macchi C, Meroni M, Lanti C, Ricci C, Maggioni M, Fracanzani A L, Badiali S, Fargion S, Magni P, Valenti L, Dongiovanni P (2016) Liver fat accumulation is associated with circulating PCSK9. Ann Med 48: 384-391

Salameh H, Hanayneh M A, Masadeh M, Naseemuddin M, Matin T, Erwin A, Singal A K (2016) PNPLA3 as a Genetic Determinant of Risk for and Severity of Non-alcoholic Fatty Liver Disease Spectrum. J Clin Transl Hepatol 4: 175-191

Scarpulla, R. C. (2002). Nuclear activators and coactivators in mammalian mitochondrial biogenesis. Biochim Biophys Acta 1576, 1-14

Sehgal, A. et al. (2015) An RNAi therapeutic targeting antithrombin to rebalance the coagulation system and promote hemostasis in hemophilia. Nat. Med. 21, 492-497

Semenza, G. L. (2011). Hypoxia-inducible factor 1: regulator of mitochondrial metabolism and mediator of ischemic preconditioning. Biochim Biophys Acta 1813, 1263-1268

Semple, S. C. et al. (2010) Rational design of cationic lipids for siRNA delivery.Nat. Biotechnol. 28, 172-176

Shaker M, Tabbaa A, Albeldawi M, Alkhouri N (2014) Liver transplantation for nonalcoholic fatty liver disease: new challenges and new opportunities. World J Gastroentero 20: 5320-5330

Shoaie S, Ghaffari P, Kovatcheva-Datchary P, Mardinoglu A, Sen P, Pujos-Guillot E, de Wouters T, Juste C, Rizkalla S, Chilloux J, Hoyles L, Nicholson J K, Dore J, Dumas M E, Clement K, Backhed F, Nielsen J (2015) Quantifying Diet-Induced Metabolic Changes of the Human Gut Microbiome. Cell Metab 22: 320-331

Subramanian A, Tamayo P, Mootha V K, Mukherjee S, Ebert B L, Gillette M A, Paulovich A, Pomeroy S L, Golub T R, Lander E S, Mesirov J P (2005) Gene set enrichment analysis: a knowledge-based approach for interpreting genome-wide expression profiles. P Natl Acad Sci USA 102: 15545-15550

Teixeira-Clerc F, Julien B, Grenard P, Tran Van Nhieu J, Deveaux V, Li L, Serriere-Lanneau V, Ledent C, Mallat A, Lotersztajn S (2006) CB1 cannabinoid receptor antagonism: a new strategy for the treatment of liver fibrosis. Nat Med 12: 671-676

Thiel, G., and Cibelli, G. (2002). Regulation of life and death by the zinc finger transcription factor Egr-1. J Cell Physio 193, 287-292

Thul P J, Akesson L, Wiking M, Mandessian D, Geladaki A, Ait Blal H, Alm T, Asplund A, Bjork L, Breckels L M, Backstrom A, Danielsson F, Fagerberg L, Fall J, Gatto L, Gnann C, Hober S, Hjelmare M, Johansson F, Lee S et al (2017) A subcellular map of the human proteome. Science Uhlen M, Fagerberg L, Hallstrom B M, Lindskog C, Oksvold P, Mardinoglu A, Sivertsson A, Kampf C, Sjostedt E, Asplund A, Lundberg E, Djureinovic D, Odeberg J, Habuka M, Tahmasebpoor S, Danielsson A, Edlund K, Szigyarto C A, Skogs M, Takanen J O et al (2015) Tissue-based map of the human proteome. Science 347: 1260419

Uhlen M, Hallstrom B M, Lindskog C, Mardinoglu A, Ponten F, Nielsen J (2016) Transcriptomics resources of human tissues and organs. Mol Syst Biol 12: 862

Varemo, L., Nielsen, J., and Nookaew, I. (2013). Enriching the gene set analysis of genome-wide data by incorporating directionality of gene expression and combining statistical hypotheses and methods. Nucleic Acids Res 41, 4378-4391

Varemo L, Scheele C, Broholm C, Mardinoglu A, Kampf C, Asplund A, Nookaew I, Uhlén M, Pedersen B K, Nielsen J (2015) Transcriptome and proteome driven reconstruction of the human myocyte metabolic model and its use for identification of metabolic markers for type 2 diabetes. Cell Rep 11: 921-933

Wang H, Chu W, Das S K, Ren Q, Hasstedt S J, Elbein S C (2002) Liver pyruvate kinase polymorphisms are associated with type 2 diabetes in northern European Caucasians. Diabetes 51: 2861-2865

Wu, C. L., Zukerberg, L. R., Ngwu, C., Harlow, E., and Lees, J. A. (1995). In vivo association of E2F and DP family proteins. Mol Cell Biol 15, 2536-2546

Yizhak K, Chaneton B, Gottlieb E, Ruppin E (2015) Modeling cancer metabolism on a genome scale. Mol Syst Biol 11: 817

Yizhak K, Gabay O, Cohen H, Ruppin E (2013) Model-based identification of drug targets that revert disrupted metabolism and its application to ageing. Nat Commun 4: 2632

Yizhak K, Gaude E, Le Devedec S, Waldman Y Y, Stein G Y, van de Water B, Frezza C, Ruppin E (2014a) Phenotype-based cell-specific metabolic modeling reveals metabolic liabilities of cancer. Elife 3: e03641

Yizhak K, Le Devedec S E, Rogkoti V M, Baenke F, de Boer V C, Frezza C, Schulze A, van de Water B, Ruppin E (2014b) A computational study of the Warburg effect identifies metabolic targets inhibiting cancer migration. Mol Syst Biol 10: 744

Younossi Z M, Koenig A B, Abdelatif D, Fazel Y, Henry L, Wymer M (2016) Global epidemiology of nonalcoholic fatty liver disease-Meta-analytic assessment of prevalence, incidence, and outcomes. Hepatology 64: 73-84

Younossi Z M, Otgonsuren M, Henry L, Venkatesan C, Mishra A, Erario M, Hunt S (2015) Association of nonalcoholic fatty liver disease (NAFLD) with hepatocellular carcinoma (HCC) in the United States from 2004 to 2009. Hepatology 62: 1723-1730

Yu, R. Z. et al. (2016a) Disposition and pharmacology of a GalNAc3-conjugated ASO targeting human lipoprotein (a) in mice. Mol. Ther. Nucleic Acids 5, e317

Yu, R. Z. et al. (2016b) Disposition and pharmacokinetics of a GalNAc3-conjugated antisense oligonucleotide targeting human lipoprotein (a) in monkeys. Nucleic Acid Ther. 26, 372-380

Zerbino, D. R., Wilder, S. P., Johnson, N., Juettemann, T., and Flicek, P. R. (2015). The ensembl regulatory build. Genome Biol 16, 56

Zhang C, Ji B, Mardinoglu A, Nielsen J, Hua Q (2015) Logical transformation of genome-scale metabolic models for gene level applications and analysis. Bioinformatics 31: 2324-2331

Zhang C, Lee S, Mardinoglu A, Hua Q (2016) Investigating the Combinatory Effects of Biological Networks on Gene Co-expression. Front Physiol 7: 160

The invention claimed is:

1. A method of treating a subject having nonalcoholic fatty liver disease (NAFLD) or hepatocellular carcinoma (HCC), said method comprising administering to the subject a therapeutically effective amount of a medical agent comprising a polynucleotide, which medical agent is capable of silencing or knocking out the pyruvate kinase liver and red blood cell (PKLR) gene.

2. The method according to claim 1, wherein the polynucleotide is an RNA molecule.

3. The method according to claim 1, wherein the polynucleotide is an anti sense polynucleotide.

4. The method according to claim 1, wherein the polynucleotide is capable of selective interaction with PKLR DNA or PKLR RNA.

5. The method according to claim 1, wherein the polynucleotide is capable of selective interaction with a sequence selected from SEQ ID NO:1, SEQ ID NO:2, SEQ ID NO:3 and SEQ ID NO:4.

6. The method according to claim 1, wherein the polynucleotide is capable of selective interaction with a RNA sequence that can be transcribed from a sequence selected from SEQ ID NO:1, SEQ ID NO:2, SEQ ID NO:3 and SEQ ID NO:4.

7. The method according to claim 1, wherein the polynucleotide comprises a sequence that is at least 75% identical to SEQ ID NO:5, SEQ ID NO:6, SEQ ID NO:7 or SEQ ID NO:8.

8. The method according to claim 1, wherein the medical agent is formulated in a lipid nanoparticle.

9. The method according to claim 1, wherein the polynucleotide is conjugated to GalNAc.

10. The method according to claim 9, wherein the polynucleotide GalNAc conjugate is a trivalent GalNAc conjugate.

11. The method according to claim 10, wherein the polynucleotide GalNAc conjugate comprises more than three GalNAc molecules per polynucleotide.

12. The method according to claim 1, wherein the 5'-phosphate of the polynucleotide is modified.

13. The method according to claim 1, wherein the polynucleotide is phosphorothioate modified.

14. The method according to claim 1, wherein the method comprises a step of detecting expression of the PKLR gene in a liver sample from the subject having the NAFLD or HCC.

15. The method according to claim 14, wherein the liver sample is a liver biopsy.

16. The method according to claim 14, wherein the step of detecting expression of the PKLR gene comprises PCR, RNA-Seq or a micro array.

17. The method of claim 1, wherein the medical agent is administered orally or by subcutaneous injection.

18. The method according to claim 2, wherein the RNA molecule is a siRNA molecule, a miRNA molecule, a guide RNA molecule (gRNA) or an aptamer.

19. The method according to claim 3, wherein the antisense polynucleotide is an antisense oligonucleotide (ASO).

20. The method according to claim 5, wherein the polynucleotide is capable of selective interaction with a sequence selected from SEQ ID NO:2 and 4.

21. The method according to claim 6, wherein the polynucleotide is capable of selective interaction with a RNA sequence that can be transcribed from a sequence selected from SEQ ID NO:2 and 4.

22. The method according to claim 9, wherein the polynucleotide is a GalNAc cluster.

23. The method according to claim 12, wherein the 5'-phosphate of the polynucleotide is modified to 5'-vinylphosphonate.

* * * * *

UNITED STATES PATENT AND TRADEMARK OFFICE

CERTIFICATE OF CORRECTION

PATENT NO. : 11,034,960 B2
APPLICATION NO. : 16/638927
DATED : June 15, 2021
INVENTOR(S) : Mardinoglu et al.

It is certified that error appears in the above-identified patent and that said Letters Patent is hereby corrected as shown below:

On the Title Page

(72) Inventors: Please correct “Uhién” to read -- Uhlén --

(30) Foreign Application Priority Data: Please correct “17186181” to read -- 17186181.8 --

In the Specification

Column 19, Line 57: Please correct “I3-oxidation” to read -- β-oxidation --

Column 22, Line 19: Please correct “Gactor” to read -- Factor --

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 18

<210> SEQ ID NO 1
<211> LENGTH: 2083
<212> TYPE: DNA
<213> ORGANISM: Homo sapiens

<400> SEQUENCE: 1

```
cattccatgg tcccgcagcc ccaggcccac actgaaagca tgtcgatcca ggagaacata     60
tcatccctgc agcttcggtc atgggtctct aagtcccaaa gagacttagc aaagtccatc    120
ctgattgggg ctccaggagg gccagcgggg tatctgcggc gggccagtgt ggcccaactg    180
acccaggagc tgggcactgc cttcttccag cagcagcagc tgccagctgc tatggcagac    240
accttcctgg aacacctctg cctactggac attgactccg agcccgtggc tgctcgcagt    300
accagcatca ttgccaccat cgggccagca tctcgctccg tggagcgcct caaggagatg    360
atcaaggccg ggatgaacat tgcgcgactc aacttctccc acggctccca cgagtaccat    420
gctgagtcca tcgccaacgt ccgggaggcg gtggagagct ttgcaggttc cccactcagc    480
taccggcccg tggccatcgc cctggacacc aagggaccgg agatccgcac tgggatcctg    540
caggggggtc cagagtcgga agtggagctg gtgaagggct cccaggtgct ggtgactgtg    600
gaccccgcgt tccggacgcg ggggaacgcg aacaccgtgt gggtggacta ccccaatatt    660
gtccgggtcg tgccggtggg gggccgcatc tacattgacg acgggctcat ctccctagtg    720
gtccagaaaa tcggcccaga gggactggtg acccaagtgg agaacggcgg cgtcctgggc    780
agccggaagg gcgtgaactt gccaggggcc caggtggact tgcccgggct gtccgagcag    840
gacgtccgag acctgcgctt cggggtggag catggggtgg acatcgtctt tgcctccttt    900
gtgcggaaag ccagcgacgt ggctgccgtc agggctgctc tgggtccgga aggacacggc    960
atcaagatca tcagcaaaat tgagaaccac gaaggcgtga agaggtttga tgaaatcctg   1020
gaggtgagcg acggcatcat ggtggcacgg ggggacctag gcatcgagat cccagcagag   1080
aaggttttcc tggctcagaa gatgatgatt gggcgctgca acttggcggg caagcctgtt   1140
gtctgtgcca cacagatgct ggagagcatg attaccaagc ccggccaac gagggcagag    1200
acaagcgatg tcgccaatgc tgtgctggat ggggctgact gcatcatgct gtcaggggag   1260
actgccaagg gcaacttccc tgtggaagcg gtgaagatgc agcatgcgat tgcccgggag   1320
gcagaggccg cagtgtacca ccggcagctg tttgaggagc tacgtcgggc agcgccacta   1380
agccgtgatc ccactgaggt caccgccatt ggtgctgtgg aggctgcctt caagtgctgt   1440
gctgctgcca tcattgtgct gaccacaact ggccgctcag cccagcttct gtctcggtac   1500
cgacctcggg cagcagtcat tgctgtcacc cgctctgccc aggctgcccg ccaggtccac   1560
ttatgccgag gagtcttccc cttgctttac cgtgaacctc cagaagccat ctgggcagat   1620
gatgtagatc gccgggtgca atttggcatt gaaagtggaa agctccgtgg cttcctccgt   1680
gttggagacc tggtgattgt ggtgacaggc tggcgacctg gctccggcta caccaacatc   1740
atgcgggtgc taagcatatc ctgagacgcc cctccctcct ctggcccagc ctacccttgt   1800
accccatccc ttcctcccca gtctacgttc tccagcccac acccctccaa agccccacct   1860
ttaagtcctc tcttctctat tcctgaccct ccctacctga ggcctatctg agactataac   1920
tgtcatctag ccccttcgag gttgcccctt ccccatctcc atttcacaca ggtcctgaaa   1980
gtctgtgtcc aattatgcac tggccaccca acagcaccaa ttgtacattc cctgcatcca   2040
atctgctcag caggccctaa gatgccttga gtctttaatc cca                      2083
```

<210> SEQ ID NO 2
<211> LENGTH: 1725
<212> TYPE: DNA
<213> ORGANISM: Homo sapiens

<400> SEQUENCE: 2

```
atgtcgatcc aggagaacat atcatccctg cagcttcggt catgggtctc taagtcccaa      60
agagacttag caaagtccat cctgattggg gctccaggag ggccagcggg gtatctgcgg     120
cgggccagtg tggcccaact gacccaggag ctgggcactg ccttcttcca gcagcagcag     180
ctgccagctg ctatggcaga caccttcctg gaacacctct gcctactgga cattgactcc     240
gagcccgtgg ctgctcgcag taccagcatc attgccacca tcgggccagc atctcgctcc     300
gtggagcgcc tcaaggagat gatcaaggcc gggatgaaca ttgcgcgact caacttctcc     360
cacggctccc acgagtacca tgctgagtcc atcgccaacg tccgggaggc ggtggagagc     420
tttgcaggtt ccccactcag ctaccggccc gtggccatcg ccctggacac caagggaccg     480
gagatccgca ctgggatcct gcagggggt  ccagagtcgg aagtggagct ggtgaagggc     540
tcccaggtgc tggtgactgt ggaccccgcg ttccggacgc gggggaacgc gaacaccgtg     600
tgggtggact accccaatat tgtccgggtc gtgccggtgg ggggccgcat ctacattgac     660
gacgggctca tctccctagt ggtccagaaa atcggcccag agggactggt gacccaagtg     720
gagaacggcg gcgtcctggg cagccggaag ggcgtgaact tgccaggggc ccaggtggac     780
ttgcccgggc tgtccgagca ggacgtccga gacctgcgct tcggggtgga gcatggggtg     840
gacatcgtct ttgcctcctt tgtgcggaaa gccagcgacg tggctgccgt cagggctgct     900
ctgggtccgg aaggacacgg catcaagatc atcagcaaaa ttgagaacca cgaaggcgtg     960
aagaggtttg atgaaatcct ggaggtgagc gacggcatca tggtggcacg gggggaccta    1020
ggcatcgaga tcccagcaga gaaggttttc ctggctcaga agatgatgat tgggcgctgc    1080
aacttggcgg gcaagcctgt tgtctgtgcc acacagatgc tggagagcat gattaccaag    1140
ccccggccaa cgagggcaga gacaagcgat gtcgccaatg ctgtgctgga tggggctgac    1200
tgcatcatgc tgtcagggga gactgccaag ggcaacttcc ctgtggaagc ggtgaagatg    1260
cagcatgcga ttgcccggga ggcagaggcc gcagtgtacc accggcagct gtttgaggag    1320
ctacgtcggg cagcgccact aagccgtgat cccactgagg tcaccgccat tggtgctgtg    1380
gaggctgcct tcaagtgctg tgctgctgcc atcattgtgc tgaccacaac tggccgctca    1440
gcccagcttc tgtctcggta ccgacctcgg gcagcagtca ttgctgtcac ccgctctgcc    1500
caggctgccc gccaggtcca cttatgccga ggagtcttcc ccttgcttta ccgtgaacct    1560
ccagaagcca tctgggcaga tgatgtagat cgccgggtgc aatttggcat tgaaagtgga    1620
aagctccgtg gcttcctccg tgttggagac ctggtgattg tggtgacagg ctggcgacct    1680
ggctccggct acaccaacat catgcgggtg ctaagcatat cctga                    1725
```

<210> SEQ ID NO 3
<211> LENGTH: 2479
<212> TYPE: DNA
<213> ORGANISM: Homo sapiens

<400> SEQUENCE: 3

```
actttaacca gtctgcagaa ctgatcccca gcccagctgg gcctcatgcc tctgacaacc      60
caacagtgtg gagcagaccc acagagaggg agacccagag aggtgtgcag tggcatggaa     120
```

```
gggccagcgg ggtatctgcg gcgggccagt gtggcccaac tgacccagga gctgggcact    180
gccttcttcc agcagcagca gctgccagct gctatggcag acaccttcct ggaacacctc    240
tgcctactgg acattgactc cgagcccgtg gctgctcgca gtaccagcat cattgccacc    300
atcgggccag catctcgctc cgtggagcgc ctcaaggaga tgatcaaggc cgggatgaac    360
attgcgcgac tcaacttctc ccacggctcc cacgagtacc atgctgagtc catcgccaac    420
gtccgggagg cggtggagag ctttgcaggt tccccactca gctaccggcc cgtggccatc    480
gccctggaca ccaagggacc ggagatccgc actgggatcc tgcagggggg tccagagtcg    540
gaagtggagc tggtgaaggg ctcccaggtg ctggtgactg tggaccccgc gttccggacg    600
cgggggaacg cgaacaccgt gtgggtggac taccccaata ttgtccgggt cgtgccggtg    660
gggggccgca tctacattga cgacgggctc atctccctag tggtccagaa aatcggccca    720
gagggactgg tgacccaagt ggagaacggc ggcgtcctgg gcagccggaa gggcgtgaac    780
ttgccagggg cccaggtgga cttgcccggg ctgtccgagc aggacgtccg agacctgcgc    840
ttcggggtgg agcatggggt ggacatcgtc tttgcctcct ttgtgcggaa agccagcgac    900
gtggctgccg tcagggctgc tctgggtccg gaaggacacg gcatcaagat catcagcaaa    960
attgagaacc acgaaggcgt gaagaggttt gatgaaatcc tggaggtgag cgacggcatc   1020
atggtggcac ggggggacct aggcatcgag atcccagcag agaaggtttt cctggctcag   1080
aagatgatga ttgggcgctg caacttggcg ggcaagcctg ttgtctgtgc cacacagatg   1140
ctggagagca tgattaccaa gccccggcca acgagggcag agacaagcga tgtcgccaat   1200
gctgtgctgg atggggctga ctgcatcatg ctgtcagggg agactgccaa gggcaacttc   1260
cctgtggaag cggtgaagat gcagcatgcg attgcccggg aggcagaggc cgcagtgtac   1320
caccggcagc tgtttgagga gctacgtcgg gcagcgccac taagccgtga tcccactgag   1380
gtcaccgcca ttggtgctgt ggaggctgcc ttcaagtgct gtgctgctgc catcattgtg   1440
ctgaccacaa ctggccgctc agcccagctt ctgtctcggt accgacctcg ggcagcagtc   1500
attgctgtca cccgctctgc ccaggctgcc cgccaggtcc acttatgccg aggagtcttc   1560
cccttgcttt accgtgaacc tccagaagcc atctgggcag atgatgtaga tcgccgggtg   1620
caatttggca ttgaaagtgg aaagctccgt ggcttcctcc gtgttggaga cctggtgatt   1680
gtggtgacag gctggcgacc tggctccggc tacaccaaca tcatgcgggt gctaagcata   1740
tcctgagacg cccctccctc ctctggccca gcctaccctt gtaccccatc ccttcctccc   1800
cagtctacgt tctccagccc acacccctcc aaagccccac ctttaagtcc tctcttctct   1860
attcctgacc ctccctacct gaggcctatc tgagactata actgtcatct agccccttcg   1920
aggttgcccc ttccccatct ccatttcaca caggtcctga aagtctgtgt ccaattatgc   1980
actggccacc caacagcacc aattgtacat tccctgcatc caatctgctc agcaggccct   2040
aagatgcctt gagtctttaa tcccagtttg gctggttaat tccataaccc caggcatccc   2100
atcccttggg gtgggggaga ggggagacag ggcaatcttg tccacagtct cccattctca   2160
tatgtagccc tcatgataat ctgggcatct cgtgccaggg caggctaccc cttcatggtg   2220
actaacagtt acatgaaagt ccacgctttt gggaaaactg ggtgggatgg atgctgggga   2280
gaagtgaggg ctgggcagct gattttgtca ctgtcttcac aacctccgtg ctgggcttgt   2340
agaccactgt cctggctgct ctcatgcctg cctgataccc tgcttggtca aatccccggc   2400
tgcttccttc tgcacccaga aattccttcc cactcatgtt gttcccacac acaaaccaag   2460
agccaaaaat gagtgtgtc                                                2479
```

<210> SEQ ID NO 4
<211> LENGTH: 1632
<212> TYPE: DNA
<213> ORGANISM: Homo sapiens

<400> SEQUENCE: 4

```
atggaagggc cagcggggta tctgcggcgg gccagtgtgg cccaactgac ccaggagctg      60

ggcactgcct tcttccagca gcagcagctg ccagctgcta tggcagacac cttcctggaa     120

cacctctgcc tactggacat tgactccgag cccgtggctg ctcgcagtac cagcatcatt     180

gccaccatcg ggccagcatc tcgctccgtg gagcgcctca aggagatgat caaggccggg     240

atgaacattg cgcgactcaa cttctcccac ggctcccacg agtaccatgc tgagtccatc     300

gccaacgtcc gggaggcggt ggagagcttt gcaggttccc cactcagcta ccggcccgtg     360

gccatcgccc tggacaccaa gggaccggag atccgcactg ggatcctgca ggggggtcca     420

gagtcggaag tggagctggt gaagggctcc caggtgctgg tgactgtgga ccccgcgttc     480

cggacgcggg ggaacgcgaa caccgtgtgg gtggactacc ccaatattgt ccgggtcgtg     540

ccggtggggg gccgcatcta cattgacgac gggctcatct ccctagtggt ccagaaaatc     600

ggcccagagg gactggtgac ccaagtggag aacggcggcg tcctgggcag ccggaagggc     660

gtgaacttgc caggggccca ggtggacttg cccgggctgt ccgagcagga cgtccgagac     720

ctgcgcttcg ggtggagca tggggtggac atcgtctttg cctcctttgt gcggaaagcc      780

agcgacgtgg ctgccgtcag ggctgctctg ggtccggaag gacacggcat caagatcatc     840

agcaaaattg agaaccacga aggcgtgaag aggtttgatg aaatcctgga ggtgagcgac     900

ggcatcatgg tggcacgggg ggacctaggc atcgagatcc cagcagagaa ggttttcctg     960

gctcagaaga tgatgattgg gcgctgcaac ttggcgggca agcctgttgt ctgtgccaca    1020

cagatgctgg agagcatgat taccaagccc cggccaacga gggcagagac aagcgatgtc    1080

gccaatgctg tgctggatgg ggctgactgc atcatgctgt caggggagac tgccaagggc    1140

aacttccctg tggaagcggt gaagatgcag catgcgattg cccgggaggc agaggccgca    1200

gtgtaccacc ggcagctgtt tgaggagcta cgtcgggcag cgccactaag ccgtgatccc    1260

actgaggtca ccgccattgg tgctgtggag gctgccttca agtgctgtgc tgctgccatc    1320

attgtgctga ccacaactgg ccgctcagcc cagcttctgt ctcggtaccg acctcgggca    1380

gcagtcattg ctgtcacccg ctctgcccag gctgcccgcc aggtccactt atgccgagga    1440

gtcttcccct tgctttaccg tgaacctcca gaagccatct gggcagatga tgtagatcgc    1500

cgggtgcaat ttggcattga aagtggaaag ctccgtggct tcctccgtgt tggagacctg    1560

gtgattgtgg tgacaggctg gcgacctggc tccggctaca ccaacatcat gcgggtgcta    1620

agcatatcct ga                                                        1632
```

<210> SEQ ID NO 5
<211> LENGTH: 21
<212> TYPE: DNA
<213> ORGANISM: Homo sapiens

<400> SEQUENCE: 5

```
ggagaugauc aaggccgggt t                                                21
```

<210> SEQ ID NO 6
<211> LENGTH: 21
<212> TYPE: DNA

<213> ORGANISM: Homo sapiens

<400> SEQUENCE: 6
cccggccuug aucaucucct t 21

<210> SEQ ID NO 7
<211> LENGTH: 21
<212> TYPE: DNA
<213> ORGANISM: Homo sapiens

<400> SEQUENCE: 7
ggacacggca ucaagaucat t 21

<210> SEQ ID NO 8
<211> LENGTH: 21
<212> TYPE: DNA
<213> ORGANISM: Homo sapiens

<400> SEQUENCE: 8
ugaucuugau gccguguoct t 21

<210> SEQ ID NO 9
<211> LENGTH: 20
<212> TYPE: DNA
<213> ORGANISM: Homo sapiens

<400> SEQUENCE: 9
ctctgatttg gtcgtattgg 20

<210> SEQ ID NO 10
<211> LENGTH: 21
<212> TYPE: DNA
<213> ORGANISM: Homo sapiens

<400> SEQUENCE: 10
gtaaaccatg tagttgaggt c 21

<210> SEQ ID NO 11
<211> LENGTH: 19
<212> TYPE: DNA
<213> ORGANISM: Homo sapiens

<400> SEQUENCE: 11
aaaattgaga accacgaag 19

<210> SEQ ID NO 12
<211> LENGTH: 20
<212> TYPE: DNA
<213> ORGANISM: Homo sapiens

<400> SEQUENCE: 12
gaataaactc caggcctatg 20

<210> SEQ ID NO 13
<211> LENGTH: 20
<212> TYPE: DNA
<213> ORGANISM: Homo sapiens

<400> SEQUENCE: 13
gagtgtctga tggggaaaac 20

<210> SEQ ID NO 14
<211> LENGTH: 21

-continued

```
<212> TYPE: DNA
<213> ORGANISM: Homo sapiens

<400> SEQUENCE: 14

tctgaaggaa ggagggataa g                                              21


<210> SEQ ID NO 15
<211> LENGTH: 17
<212> TYPE: DNA
<213> ORGANISM: Homo sapiens

<400> SEQUENCE: 15

caagtgtgca gtcatgg                                                   17


<210> SEQ ID NO 16
<211> LENGTH: 18
<212> TYPE: DNA
<213> ORGANISM: Homo sapiens

<400> SEQUENCE: 16

caagtgtgac agtcatgg                                                  18


<210> SEQ ID NO 17
<211> LENGTH: 20
<212> TYPE: DNA
<213> ORGANISM: Homo sapiens

<400> SEQUENCE: 17

ctctgatttg gtcgtattgg                                                20


<210> SEQ ID NO 18
<211> LENGTH: 21
<212> TYPE: DNA
<213> ORGANISM: Homo sapiens

<400> SEQUENCE: 18

gtaaaccatg tagttgaggt c                                              21
```